US008628952B2

(12) United States Patent
Stuelpnagel et al.

(10) Patent No.: US 8,628,952 B2
(45) Date of Patent: *Jan. 14, 2014

(54) ARRAY KITS AND PROCESSING SYSTEMS

(75) Inventors: John R. Stuelpnagel, Encinitas, CA (US); Mark S. Chee, Encinitas, CA (US); Steven R. Auger, Cohasset, MA (US); Gan G. Wang, San Diego, CA (US); Laura S. Casas, Chula Vista, CA (US); Shawn Christopher Baker, San Diego, CA (US); Robert C. Kain, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 235 days.

This patent is subject to a terminal disclaimer.

(21) Appl. No.: 12/405,162

(22) Filed: Mar. 16, 2009

(65) Prior Publication Data

US 2009/0215649 A1 Aug. 27, 2009

Related U.S. Application Data

(63) Continuation of application No. 10/767,249, filed on Jan. 28, 2004, now Pat. No. 7,510,841, which is a continuation of application No. 09/606,369, filed on Jun. 28, 2000, now abandoned.

(51) Int. Cl.
*C12M 1/34* (2006.01)
*C12M 3/00* (2006.01)
*G01N 15/06* (2006.01)
*G01N 21/00* (2006.01)
*G01N 33/543* (2006.01)
*C07H 21/02* (2006.01)
*C07H 21/04* (2006.01)

(52) U.S. Cl.
USPC ... 435/287.2; 435/6.1; 435/283.1; 435/288.3; 435/288.4; 435/288.7; 422/68.1; 422/82.05; 436/518; 536/23.1; 536/24.3

(58) Field of Classification Search
USPC .............. 435/6.1, 283.1, 287.2, 288.3, 288.4, 435/288.7; 422/68.1, 82.05; 436/518; 536/23.1, 24.3
See application file for complete search history.

(56) References Cited

U.S. PATENT DOCUMENTS

| | | | |
|---|---|---|---|
| 3,281,860 A | 10/1966 | Adams | |
| 3,690,836 A | 9/1972 | Buissiere | |
| 3,710,933 A | 1/1973 | Fulwyler | |
| 3,802,966 A | 4/1974 | Delekto | |
| 4,016,855 A | 4/1977 | Mimata | |
| 4,121,222 A | 10/1978 | Diebold | |
| 4,200,110 A | 4/1980 | Peterson et al. | |
| 4,204,929 A | 5/1980 | Bier | |
| 4,349,510 A | 9/1982 | Kolehmainen et al. | |
| 4,373,071 A | 2/1983 | Itakura | |
| 4,458,066 A | 7/1984 | Caruthers | |
| 4,499,052 A | 2/1985 | Fulwyer | |
| 4,500,707 A | 2/1985 | Caruthers | |
| 4,672,040 A | 6/1987 | Josephson | |
| 4,682,895 A | 7/1987 | Costello | |
| 4,707,454 A | 11/1987 | Hendrix | |
| 4,728,502 A | 3/1988 | Hamill | |
| 4,731,325 A | 3/1988 | Palva | |
| 4,780,504 A | 10/1988 | Buenadia | |
| 4,785,814 A | 11/1988 | Kane | |
| 4,812,512 A | 3/1989 | Buenadia | |
| 4,815,274 A | 3/1989 | Piatti | |
| 4,822,746 A | 4/1989 | Walt | |
| 4,824,789 A | 4/1989 | Yafuso et al. | |
| 4,853,335 A | 8/1989 | Olson | |
| 4,877,745 A | 10/1989 | Hayes | |
| 4,878,971 A | 11/1989 | Tsunekawa | |
| 4,879,097 A | 11/1989 | Whitehead et al. | |
| 4,895,706 A | 1/1990 | Root et al. | |
| 4,922,092 A | 5/1990 | Rushbrooke et al. | |
| 4,963,498 A | 10/1990 | Hillman | |
| 4,992,383 A | 2/1991 | Farnsworth | |
| 4,999,306 A | 3/1991 | Yafuso et al. | |
| 5,002,867 A | 3/1991 | Macevicz | |
| 5,021,550 A | 6/1991 | Zeiger | |
| 5,028,545 A | 7/1991 | Soini | |
| 5,047,524 A | 9/1991 | Andrus | |
| 5,073,029 A | 12/1991 | Eberly et al. | |
| 5,087,820 A | 2/1992 | Kearns | |
| 5,100,775 A | 3/1992 | Smyczek et al. | |
| 5,105,305 A | 4/1992 | Betzig et al. | |

(Continued)

FOREIGN PATENT DOCUMENTS

| | | |
|---|---|---|
| CA | 2 305 545 | 4/1999 |
| CA | 2 335 951 | 12/1999 |

(Continued)

OTHER PUBLICATIONS

Datasheet Array, Retrieved from the internet URL:http//dictionary.reference.com/browse/array, printed Sep. 3, 2010.*
Datasheet Plate, Retrieved from the internet URL:http//dictionary.reference.com/browse/plate, printed Sep. 3, 2010.*
96 well plate dimensions, down loaded from the internet (http://catalog2.corning.com), printed Jul. 8, 2011, p. 1.*
Lachenal, Dispersive and fourier transform near infra red spectroscopy of polymeric materials, 1995, Vibrational Spectroscopy, 9, 93-100.*
Decision of the Technical Board of Appeal 3.3.04 of Jun. 26, 2009, Case No. T 0384/08-3304.
Geysen et al., Strategies for Epitope Analysis Using Peptide Synthesis, Journal of Immunology Methods, 1987, vol. 102, pp. 259-274.
Kwiatkowski, et al., A High-Capacity Manifold Support for the Detection of Specific IgE Antibodies in Allergic Individuals, Journal of Immunology Methods, 1994, vol. 168, pp. 137-143.

(Continued)

*Primary Examiner* — Narayan Bhat
(74) *Attorney, Agent, or Firm* — Knobbe, Martens, Olson & Bear, LLP

(57) ABSTRACT

The invention relates to sensor compositions comprising a composite array of individual arrays, to allow for simultaneous processing of a number of samples. The invention further provides methods of making and using the composite arrays. The invention further provides a hybridization chamber for use with a composite array.

70 Claims, 13 Drawing Sheets

(56) References Cited

U.S. PATENT DOCUMENTS

| | | |
|---|---|---|
| 5,114,864 A | 5/1992 | Walt |
| 5,126,276 A | 6/1992 | Fish et al. |
| 5,132,242 A | 7/1992 | Cheung |
| 5,141,813 A | 8/1992 | Nelson |
| 5,143,853 A | 9/1992 | Walt |
| 5,143,854 A | 9/1992 | Pirrung |
| 5,144,136 A | 9/1992 | Kubisiak |
| 5,153,319 A | 10/1992 | Caruthers |
| 5,176,881 A | 1/1993 | Sepaniak |
| 5,188,963 A | 2/1993 | Stapleton |
| 5,194,300 A | 3/1993 | Cheung |
| 5,200,051 A | 4/1993 | Cozzette |
| 5,204,253 A | 4/1993 | Sanford |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,256,549 A | 10/1993 | Urdea |
| 5,278,048 A | 1/1994 | Parce et al. |
| 5,281,516 A | 1/1994 | Stapleton |
| 5,281,540 A | 1/1994 | Merkh |
| 5,287,272 A | 2/1994 | Rutenberg |
| 5,288,514 A | 2/1994 | Ellman |
| 5,298,741 A | 3/1994 | Walt et al. |
| 5,300,779 A | 4/1994 | Hillman |
| 5,302,509 A | 4/1994 | Cheeseman |
| 5,304,487 A | 4/1994 | Wilding |
| 5,310,469 A | 5/1994 | Cunningham |
| 5,314,829 A | 5/1994 | Coles |
| 5,320,808 A | 6/1994 | Holen |
| 5,320,814 A | 6/1994 | Walt et al. |
| 5,322,799 A | 6/1994 | Miller |
| 5,324,633 A | 6/1994 | Fodor et al. |
| 5,342,581 A | 8/1994 | Sanadi |
| 5,346,672 A | 9/1994 | Stapleton |
| 5,357,590 A | 10/1994 | Auracher |
| 5,358,691 A | 10/1994 | Clark |
| 5,374,395 A | 12/1994 | Robinson |
| 5,380,489 A | 1/1995 | Sutton et al. |
| 5,382,511 A | 1/1995 | Stapleton |
| 5,384,261 A | 1/1995 | Winkler |
| 5,435,724 A | 7/1995 | Goodman et al. |
| 5,436,129 A | 7/1995 | Stapleton |
| 5,445,970 A | 8/1995 | Rohr |
| 5,447,837 A | 9/1995 | Urnovitz |
| 5,451,500 A | 9/1995 | Stapleton |
| 5,481,629 A | 1/1996 | Tabuchi |
| 5,494,798 A | 2/1996 | Gerdt et al. |
| 5,496,997 A | 3/1996 | Pope |
| 5,512,490 A | 4/1996 | Walt et al. |
| 5,516,635 A | 5/1996 | Ekins et al. |
| 5,518,883 A | 5/1996 | Soini |
| 5,545,531 A | 8/1996 | Rava et al. |
| 5,549,974 A | 8/1996 | Holmes |
| 5,565,324 A | 10/1996 | Still et al. |
| 5,573,909 A | 11/1996 | Singer et al. |
| 5,575,849 A | 11/1996 | Honda et al. |
| 5,595,915 A | 1/1997 | Geysen |
| 5,618,701 A | 4/1997 | Landegren |
| 5,633,972 A | 5/1997 | Walt et al. |
| 5,639,603 A | 6/1997 | Dower et al. |
| 5,649,576 A | 7/1997 | Kirk |
| 5,656,241 A | 8/1997 | Seifert et al. |
| 5,674,698 A | 10/1997 | Zarling |
| 5,682,232 A | 10/1997 | Tajima et al. |
| 5,690,894 A | 11/1997 | Pinkel et al. |
| 5,759,784 A | 6/1998 | Asp et al. |
| 5,770,157 A | 6/1998 | Cargill |
| 5,784,152 A | 7/1998 | Heffelfinger et al. |
| 5,800,992 A | 9/1998 | Fodor et al. |
| 5,804,384 A | 9/1998 | Muller et al. |
| 5,807,522 A | 9/1998 | Brown et al. |
| 5,814,524 A | 9/1998 | Walt et al. |
| 5,837,196 A | 11/1998 | Pinkel |
| 5,837,860 A | 11/1998 | Anderson et al. |
| 5,840,256 A | 11/1998 | Demers et al. |
| 5,843,767 A | 12/1998 | Beattie |
| 5,854,684 A | 12/1998 | Stabile et al. |
| 5,863,708 A | 1/1999 | Zanzucchi et al. |
| 5,863,722 A | 1/1999 | Brenner |
| 5,874,219 A | 2/1999 | Rava |
| 5,876,946 A | 3/1999 | Burbaum et al. |
| 5,888,723 A | 3/1999 | Sutton et al. |
| 5,888,834 A | 3/1999 | Ishikawa et al. |
| 5,900,481 A | 5/1999 | Lough et al. |
| 5,922,617 A | 7/1999 | Wang et al. |
| 5,981,180 A | 11/1999 | Chandler |
| 6,023,540 A | 2/2000 | Walt et al. |
| 6,037,186 A | 3/2000 | Stimpson |
| 6,071,748 A | 6/2000 | Modin |
| 6,074,614 A | 6/2000 | Hafemam |
| 6,083,763 A | 7/2000 | Balch |
| 6,132,685 A | 10/2000 | Kercso et al. |
| 6,165,778 A | 12/2000 | Kedar |
| 6,191,852 B1 | 2/2001 | Paffhausen et al. |
| 6,210,910 B1 | 4/2001 | Walt et al. |
| 6,232,066 B1 | 5/2001 | Felder et al. |
| 6,268,131 B1* | 7/2001 | Kang et al. ............ 435/6 |
| 6,269,846 B1 | 8/2001 | Overbeck et al. |
| 6,327,410 B1 | 12/2001 | Walt et al. |
| 6,340,588 B1 | 1/2002 | Nova et al. |
| 6,355,431 B1 | 3/2002 | Chee |
| 6,361,940 B1* | 3/2002 | Van Ness et al. .......... 435/6 |
| 6,396,995 B1 | 5/2002 | Stuelpnagel |
| 6,406,845 B1 | 6/2002 | Walt et al. |
| 6,429,027 B1* | 8/2002 | Chee et al. ............. 436/518 |
| 6,458,533 B1 | 10/2002 | Felder et al. |
| 6,514,768 B1* | 2/2003 | Guire et al. ............ 436/518 |
| 6,519,032 B1 | 2/2003 | Kuebler et al. |
| 6,544,732 B1 | 4/2003 | Chee et al. |
| 6,551,817 B2 | 4/2003 | Besemer |
| 6,604,902 B2 | 8/2003 | Norris et al. |
| 6,620,584 B1 | 9/2003 | Chee |
| 6,646,272 B2 | 11/2003 | Rushbrooke et al. |
| 6,660,233 B1 | 12/2003 | Coassin et al. |
| 6,663,832 B2 | 12/2003 | Lebl |
| 6,770,441 B2 | 8/2004 | Dickinson et al. |
| 6,858,394 B1 | 2/2005 | Chee et al. |
| 6,890,741 B2 | 5/2005 | Fan |
| 6,991,939 B2 | 1/2006 | Walt |
| 6,998,274 B2 | 2/2006 | Chee et al. |
| 7,060,431 B2 | 6/2006 | Chee et al. |
| 7,115,884 B1 | 10/2006 | Walt et al. |
| 7,142,290 B2 | 11/2006 | Tsien et al. |
| 2002/0150909 A1 | 10/2002 | Stuelpnagel |
| 2002/0177141 A1 | 11/2002 | Chee |
| 2003/0032204 A1 | 2/2003 | Walt et al. |
| 2003/0096239 A1 | 5/2003 | Gunderson |
| 2003/0108867 A1 | 6/2003 | Chee |
| 2003/0108900 A1 | 6/2003 | Oliphant |
| 2003/0162210 A1 | 8/2003 | Chetverin |
| 2005/0158702 A1 | 7/2005 | Stuelpnagel et al. |
| 2006/0034913 A1 | 2/2006 | Gaede et al. |

FOREIGN PATENT DOCUMENTS

| | | |
|---|---|---|
| EP | 0 260 965 | 3/1988 |
| EP | 0 269 764 | 6/1988 |
| EP | 0 378 968 | 7/1990 |
| EP | 0 392 546 | 10/1990 |
| EP | 0 417 305 | 3/1991 |
| EP | 0 478 319 | 4/1992 |
| EP | 0 234 612 | 11/1992 |
| EP | 0 723 146 | 7/1995 |
| EP | 1 141 712 | 6/2000 |
| EP | 1593967 | 11/2005 |
| GB | 2 315 131 | 1/1998 |
| GB | 2 349 349 | 11/2000 |
| WO | WO 89/10977 | 11/1989 |
| WO | WO 89/11101 | 11/1989 |
| WO | WO 90/00626 | 1/1990 |
| WO | WO 90/03382 | 4/1990 |
| WO | WO 90/15070 | 12/1990 |

(56) References Cited

FOREIGN PATENT DOCUMENTS

| | | |
|---|---|---|
| WO | WO 92/10092 | 6/1992 |
| WO | WO 92/10587 | 6/1992 |
| WO | WO 92/10588 | 6/1992 |
| WO | WO 93/02360 | 2/1993 |
| WO | WO 93/06121 | 4/1993 |
| WO | WO 93/09668 | 5/1993 |
| WO | WO 93/11262 | 6/1993 |
| WO | WO 93/17126 | 9/1993 |
| WO | WO 93/22053 | 11/1993 |
| WO | WO 93/22058 | 11/1993 |
| WO | WO 93/33053 | 11/1993 |
| WO | WO 94/11388 | 5/1994 |
| WO | WO 95/20164 | 7/1995 |
| WO | WO 96/03212 | 2/1996 |
| WO | WO 97/14028 | 4/1997 |
| WO | WO 97/14928 | 4/1997 |
| WO | WO 97/26539 | 7/1997 |
| WO | WO 97/27326 | 7/1997 |
| WO | WO 97/33737 | 9/1997 |
| WO | WO 97/40385 | 10/1997 |
| WO | WO 98/08092 | 2/1998 |
| WO | WO 98/20019 | 5/1998 |
| WO | WO 98/29736 | 7/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 99/05320 | 2/1999 |
| WO | WO 99/18434 | 4/1999 |
| WO | WO 99/60170 | 11/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/16101 | 3/2000 |
| WO | WO 00/29619 | 5/2000 |
| WO | WO 00/39587 | 7/2000 |
| WO | WO 00/47996 | 8/2000 |
| WO | WO 00/48000 | 8/2000 |
| WO | WO 00/71992 | 11/2000 |
| WO | WO 01/59432 | 8/2001 |
| WO | WO 02/00336 | 1/2002 |

OTHER PUBLICATIONS

Opposition Brief filed Mar. 31, 2010 against European Patent No. 1 593 967.
Exhibit to Illumina, Inc.'s Second Amended Complaint for Patent Infringement, Patent No. 7,510,841, filed in the United States District Court for the Western District of Wisconsin in connection with Civil Action No. 09-cv-277-bbc, Aug. 14, 2009.
Letter dated Apr. 20, 2006 and corresponding attachments filed on behalf of Opponent in connection with the Opposition of European Patent EP 1141712.
Letter dated Dec. 7, 2006 and corresponding attachments filed on behalf of Proprietor in connection with the Opposition of European Patent EP 1141712.
Letter dated Oct. 29, 2008 and corresponding attachments filed on behalf of Opponent in connection with the Opposition of European Patent EP 1141712.
Letter dated Sep. 22, 2008 and corresponding attachments filed on behalf of Proprietor in connection with the Opposition of European Patent EP 1141712.
Letter dated Sep. 24, 2008 and corresponding attachments filed on behalf of Opponent in connection with the Opposition of European Patent EP 1141712.
Letter from the Opposition Division dated Feb. 8, 2008 in connection with the Opposition of European Patent EP 1141712.
Affymetrix Inc., Amended Answer to Amended Complain, filed in the United States District Court for the Western District of Wisconsin in connection with Civil Action No. 09-cv-277-bbc, Jul. 20, 2009.
Illumina, Inc., Illumina, Inc.'s Responses to Affymetrix, Inc.'s First Set of Interrogatories (Nos. 1-8), filed in the United States District Court for the Western District of Wisconsin in connection with Civil Action No. 09-cv-277-bbc, Aug. 21, 2009.
Illumina, Inc. Second Amended Complaint for Patent Infringement, filed in the United States District Court for the Western District of Wisconsin in connection with Civil Action No. 09-cv-277-bbc, Aug. 14, 2009.
Defendant Affymetrix, Inc.'s Supplemental Response to Plaintiff's First Set of Interrogatories (Nos. 3-5), United States District Court for the Western District of Wisconsin, Civil Action No. 09-cv-277-bbc, Oct. 31, 2009.
Illumina, Inc's First Set of Request for the Production of Documents and Tangible Things (Nos. 1-53) to Affymetrix, Inc., in the matter *Illumina, Inc.* v. *Affymetrix, Inc.*, U.S. District Court for the Western District of Wisconsin, Docket No. 09-cv-277-bbc, dated Jul. 2, 2009.
Illumina, Inc's First Set of Interrogatories (Nos. 1-8) to Affymetrix, Inc., in the matter *Illumina, Inc.* v. *Affymetrix, Inc.*, U.S. District Court for the Western District of Wisconsin, Docket No. 09-cv-277-bbc, dated Jul. 2, 2009.
Illumina Inc's First Set of Requests for Admission (Nos. 1-196) to Affymetrix, Inc. and Exhibit A, in the matter *Illumina, Inc.* v. *Affymetrix, Inc.*, U.S. District Court for the Western District of Wisconsin, Docket No. 09-cv-277-bbc, dated Jul. 13, 2009.
Illumina, Inc's Second Set of Request for Admission (Nos. 197-228) to Affymetrix, Inc., in the matter *Illumina, Inc.* v. *Affymetrix, Inc.*, U.S. District Court for the Western District of Wisconsin, Docket No. 09-cv-277-bbc, dated Jul. 14, 2009.
Affymetrix, Inc's Initial Disclosures, in the matter *Illumina, Inc.* v. *Affymetrix, Inc.*, U.S. District Court for the Western District of Wisconsin, Docket No. 09-cv-277-bbc, dated Jul. 31, 2009.
Illumina, Inc's Initial Disclosures Pursuant to Rule 26(a)(1), in the matter *Illumina, Inc.* v. *Affymetrix, Inc.*, U.S. District Court for the Western District of Wisconsin, Docket No. 09-cv-277-bbc, dated Jul. 31, 2009.
Affymetrix, Inc's Response to Plaintiff's First Set of Requests for Production (Nos. 1-53), in the matter *Illumina, Inc.* v. *Affymetrix, Inc.*, U.S. District Court for the Western District of Wisconsin, Docket No. 09-cv-277-bbc, dated Aug. 3, 2009.
Affymetrix, Inc's Response to Plaintiff's First Set of Interrogatories (Nos. 1-8), in the matter *Illumina, Inc.* v. *Affymetrix, Inc.*, U.S. District Court for the Western District of Wisconsin, Docket No. 09-cv-277- bbc, dated Aug. 3, 2009.
Illumina, Inc's Responses to Affymetrix, Inc's First Set of Requests for Production (Nos. 1-73), in the matter *Illumina, Inc.* v. *Affymetrix, Inc.*, U.S. District Court for the Western District of Wisconsin, Docket No. 09-cv-277-bbc, dated Aug. 21, 2009.
Illumina, Inc's Supplemented Responses to Affymetrix, Inc's First Set of Interrogatories (Nos. 1-8), in the matter *Illumina, Inc.* v. *Affymetrix, Inc.*, U.S. District Court for the Western District of Wisconsin, Docket No. 09-cv-277-bbc, dated Sep. 1, 2009.
Illumina, Inc's Second Set of Interrogatories (Nos. 9-12) to Affymetrix, Inc., in the matter *Illumina, Inc.* v. *Affymetrix, Inc.*, U.S. District Court for the Western District of Wisconsin, Docket No. 09-cv-277-bbc, dated Sep. 23, 2009.
Affymetrix, Inc's Response to Plaintiff's Second Set of Interrogatories (Nos. 9-12), in the matter *Illumina, Inc.* v. *Affymetrix, Inc.*, U.S. District Court for the Western District of Wisconsin, Docket No. 09-cv-277-bbc, dated Oct. 23, 2009.
Illumina, Inc's Third Set of Requests for Admission (Nos. 229-422) to Affymetrix, Inc., in the matter *Illumina, Inc.* v. *Affymetrix, Inc.*, U.S. District Court for the Western District of Wisconsin, Docket No. 09-cv-277-bbc, dated Jan. 15, 2010.
Illumina, Inc's First Set of Requests for the Production of Documents and Tangible Things (Nos. 1-47) to Affymetrix, Inc, in the matter *Illumina, Inc.* v. *Affymetrix, Inc.*, U.S. District Court for the Western District of Wisconsin, Docket No. 09-cv-665-bbc, dated Feb. 10, 2010.
Illumina Inc's First Set of Interrogatories (Nos. 1-5) to Affymetrix, Inc., in the matter *Illumina, Inc.* v. *Affymetrix, Inc.*, U.S. District Court for the Western District of Wisconsin, Docket No. 09-cv-665-bbc, dated Feb. 10, 2010.
Affymetrix, Inc's Response to Plaintiff's Third Set of Requests for Admission (Nos. 229-422), in the matter *Illumina, Inc.* v. *Affymetrix,*

(56) References Cited

OTHER PUBLICATIONS

*Inc.*, U.S. District Court for the Western District of Wisconsin, Docket No. 09-cv-277-bbc, dated Feb. 16, 2010.

Affymetrix, Inc's Response to Plaintiff Illumina, Inc's First Set of Interrogatories (Nos. 1-5), in the matter *Illumina, Inc. v. Affymetrix, Inc.*, U.S. District Court for the Western District of Wisconsin, Docket No. 09-cv-277-bbc, dated Mar. 12, 2010.

Affymetrix, Inc's Response to Plaintiff Illumina, Inc's First Set of Requests for the Production of Documents and Tangible Things (Nos. 1-47), in the matter *Illumina, Inc. v. Affymetrix, Inc.*, U.S. District Court for the Western District of Wisconsin, Docket No. 09-cv-277-bbc, dated Mar. 12, 2010.

Affymetrix, Inc's First Supplemental Response to Plaintiff Illumina Inc's First Set of Interrogatories (Consolidated) (Nos. 1-3), in the matter *Illumina, Inc. v. Affymetrix, Inc.*, U.S. District Court for the Western District of Wisconsin, Docket No. 09-cv-277-bbc, dated Mar. 26, 2010.

Affymetrix's Second Set of Interrogatories, in the matter *Illumina, Inc. v. Affymetrix, Inc.*, U.S. District Court for the Western District of Wisconsin, Docket No. 09-cv-277-bbc, dated Mar. 26, 2010.

Affymetrix's Second Set of Requests for Production, in the matter *Illumina, Inc. v. Affymetrix, Inc.*, U.S. District Court for the Western District of Wisconsin, Docket No. 09-cv-277-bbc, dated Mar. 26, 2010.

Illumina Inc's Responses to Affymetrix Inc's Second Set of Interrogatories (Nos. 9-16) and Exhibits A-F, in the matter *Illumina, Inc. v. Affymetrix, Inc.*, U.S. District Court for the Western District of Wisconsin, Docket No. 09-cv-277-bbc, dated Apr. 30, 2010.

Exhibit G filed in Illumina Inc's Responses to Affymetrix Inc's Second Set of Interrogatories (Nos. 9-16), in the matter *Illumina, Inc. v. Affymetrix, Inc.*, U.S. District Court for the Western District of Wisconsin, Docket No. 09-cv-277-bbc, dated Apr. 30, 2010.

Exhibits H-N filed in Illumina Inc's Responses to Affymetrix Inc's Second Set of Interrogatories (Nos. 9-16), in the matter *Illumina, Inc. v. Affymetrix, Inc.*, U.S. District Court for the Western District of Wisconsin, Docket No. 09-cv-277-bbc, dated Apr. 30, 2010.

Illumina, Inc's Responses to Affymetrix, Inc's Second Set of Requests for Production (Nos. 74-131), in the matter *Illumina, Inc. v. Affymetrix, Inc.*, U.S. District Court for the Western District of Wisconsin, Docket No. 09-cv-277-bbc, dated Apr. 30, 2010.

Affymetrix, Inc's Second Supplemental Response to Plaintiff's First Set of Interrogatories (09-665) (Nos. 1-2), in the matter *Illumina, Inc. v. Affymetrix, Inc.*, U.S. District Court for the Western District of Wisconsin, Docket No. 09-cv-277-bbc, dated Jun. 14, 2010.

Affymetrix, Inc's Supplemental Reponses to Plaintiff's First and Second Sets of Interrogatories (Nos. 3-4, 11-12), in the matter *Illumina, Inc. v. Affymetrix, Inc.*, U.S. District Court for the Western District of Wisconsin, Docket No. 09-cv-277-bbc, dated Jun. 15, 2010.

Affymetrix's Third Set of Requests for Production, in the matter *Illumina, Inc. v. Affymetrix, Inc.*, U.S. District Court for the Western District of Wisconsin, Docket No. 09-cv-277-bbc, dated Jun. 30, 2010.

Affymetrix, Inc's Supplemental Initial Disclosures, in the matter *Illumina, Inc. v. Affymetrix, Inc.*, U.S. District Court for the Western District of Wisconsin, Docket No. 09-cv-277-bbc, dated Jul. 19, 2010.

Illumina Inc's Reponses to Affymetrix, Inc's Third Set of Requests for Production (Nos. 132-142), in the matter *Illumina, Inc. v. Affymetrix, Inc.*, U.S. District Court for the Western District of Wisconsin, Docket No. 09-cv-277-bbc, dated Jul. 30, 2010.

Affymetrix, Inc's Third Supplemental Response to Plaintiff's First Set of Interrogatories (09-665) (Nos. 1-2), in the matter *Illumina, Inc. v. Affymetrix, Inc.*, U.S. District Court for the Western District of Wisconsin, Docket No. 09-cv-277-bbc, dated Aug. 2, 2010.

Affymetrix, Inc's Fourth Supplemental Response to Plaintiff's First Set of Interrogatories (09-665) (Nos. 3-4), in the matter *Illumina, Inc. v. Affymetrix, Inc.*, U.S. District Court for the Western District of Wisconsin, Docket No. 09-cv-277-bbc, dated Aug. 2, 2010.

Illumina Inc's Supplemental Responses to Affymetrix Inc's First Set of Interrogatories (Nos. 1-8) and Exhibit A-G, in the matter *Illumina, Inc. v. Affymetrix, Inc.*, U.S. District Court for the Western District of Wisconsin, Docket No. 09-cv-277-bbc, dated Sep. 15, 2010.

Exhibits H-I filed in Illumina Inc's Supplemental Responses to Affymetrix Inc's First Set of Interrogatories (Nos. 1-8), in the matter *Illumina, Inc. v. Affymetrix, Inc.*, U.S. District Court for the Western District of Wisconsin, Docket No. 09-cv-277-bbc, dated Sep. 15, 2010.

Exhibit J filed in Illumina Inc's Supplemental Responses to Affymetrix Inc's First Set of Interrogatories (Nos. 1-8), in the matter *Illumina, Inc. v. Affymetrix, Inc.*, U.S. District Court for the Western District of Wisconsin, Docket No. 09-cv-277-bbc, dated Sep. 15, 2010.

Exhibits K-Q filed in Illumina Inc's Supplemental Responses to Affymetrix Inc's First Set of Interrogatories (Nos. 1-8), in the matter *Illumina, Inc. v. Affymetrix, Inc.*, U.S. District Court for the Western District of Wisconsin, Docket No. 09-cv-277-bbc, dated Sep. 15, 2010.

Illumina Inc's Supplemental Responses to Affymetrix Inc's Second Set of Interrogatories (Nos. 9-16) and Exhibits A-F, in the matter *Illumina, Inc. v. Affymetrix, Inc.*, U.S. District Court for the Western District of Wisconsin, Docket No. 09-cv-277-bbc, dated Sep. 15, 2010.

Exhibit G filed in Illumina Inc's Supplemental Responses to Affymetrix Inc's Second Set of Interrogatories (Nos. 9-16), in the matter *Illumina, Inc. v. Affymetrix, Inc.*, U.S. District Court for the Western District of Wisconsin, Docket No. 09-cv-277-bbc, dated Sep. 15, 2010.

Exhibits H-N filed in Illumina Inc's Supplemental Responses to Affymetrix Inc's Second Set of Interrogatories (Nos. 9-16), in the matter *Illumina, Inc. v. Affymetrix, Inc.*, U.S. District Court for the Western District of Wisconsin, Docket No. 09-cv-277-bbc, dated Sep. 15, 2010.

Illumina, Inc's Initial Claim Chart, in the matter *Illumina, Inc. v. Affymetrix, Inc.*, U.S. District Court for the Western District of Wisconsin, Docket No. 09-cv-277-bbc, dated Jul. 31, 2009.

Illumina, Inc's First Amended Claim Chart, in the matter *Illumina, Inc. v. Affymetrix, Inc.*, U.S. District Court for the Western District of Wisconsin, Docket No. 09-cv-277-bbc, dated Aug. 14, 2009.

Illumina, Inc's First Amended Claim Chart, and Exhibits A-J, in the matter *Illumina, Inc. v. Affymetrix, Inc.*, U.S. District Court for the Western District of Wisconsin, Docket No. 09-cv-277-bbc, dated Sep. 1, 2009.

Certificate of Service, in the matter *Illumina, Inc. v. Affymetrix, Inc.*, U.S. District Court for the Western District of Wisconsin, Docket No. 09-cv-277-bbc, dated Dec. 9, 2009.

Illumina Inc's Claim Charts Regarding U.S. Patent No. 7,612,020, and Exhibits A-F, in the matter *Illumina, Inc. v. Affymetrix, Inc.*, U.S. District Court for the Western District of Wisconsin, Docket No. 09-cv-277-bbc, dated Dec. 9, 2009.

Exhibit G filed with Illumina Inc's Claim Charts Regarding U.S. Patent No. 7,612,020, in the matter *Illumina, Inc. v. Affymetrix, Inc.*, U.S. District Court for the Western District of Wisconsin, Docket No. 09-cv-277-bbc, dated Dec. 9, 2009.

Exhibits H-K filed with Illumina Inc's Claim Charts Regarding U.S. Patent No. 7,612,020, in the matter *Illumina, Inc. v. Affymetrix, Inc.*, U.S. District Court for the Western District of Wisconsin, Docket No. 09-cv-277-bbc, dated Dec. 9, 2009.

Illumina's Motion to Compel Production of Documents Withheld by Gregory Kirk and Supporting Memorandum, in the matter *Illumina, Inc. v. Affymetrix, Inc.*, U.S. District Court for the Northern District of California (Consolidated Actions in the Western District of Wisconsin, Docket Nos. 09-cv-277-bbc; 09-cv-665-bbc), dated Sep. 10, 2010.

Illumina's Motion for Admisitrative Relief Pursuant to Civil L.R. 7-11 and 79-5(d), in the matter *Illumina, Inc. v. Affymetrix, Inc.*, U.S. District Court for the Northern District of California (Consolidated Actions in the Western District of Wisconsin, Docket Nos. 09-cv-277-bbc; 09-cv-665-bbc), dated Sep. 10, 2010.

Certificate of Service, in the matter *Illumina, Inc. v. Affymetrix, Inc.*, U.S. District Court for the Northern District of California (Consoli-

(56) References Cited

OTHER PUBLICATIONS dated Actions in the Western District of Wisconsin, Docket Nos. 09-cv-277-bbc; 09-cv-665-bbc), dated Sep. 10, 2010.
Proposed Order Granting Illumina's Motion to Compel Production of Documents Withheld by Gregory Kirk, in the matter *Illumina, Inc.* v. *Affymetrix, Inc.*, U.S. District Court for the Northern District of California (Consolidated Actions in the Western District of Wisconsin, Docket Nos. 09-cv-277-bbc, 09- cv-665-bbc), dated Sep. 10, 2010.
Illumina Inc's Disclosure of Corporate Affiliations and Financial Interest, in the matter *Illumina, Inc.* v. *Affymetrix, Inc.*, U.S. District Court for the Western District of Wisconsin, Docket No. 09-cv-277-bbc, dated May 4, 2009.
Complaint for Patent Infringement, in the matter *Illumina, Inc.* v. *Affymetrix, Inc.*, U.S. District Court for the Western District of Wisconsin, Docket No. 09-cv-277-bbc, dated May 4, 2009.
Exhibit A in Complaint for Patent Infringement, in the matter *Illumina, Inc.* v. *Affymetrix, Inc.*, U.S. District Court for the Western District of Wisconsin, Docket No. 09-cv-277-bbc, dated May 4, 2009.
Civil Cover Sheet in Complaint for Patent Infringement, in the matter *Illumina, Inc.* v. *Affymetrix, Inc.*, U.S. District Court for the Western District of Wisconsin, Docket No. 09-cv-277-bbc, dated May 4, 2009.
Summons in a Civil Action, in the matter *Illumina, Inc.* v. *Affymetrix, Inc.*, U.S. District Court for the Western District of Wisconsin, Docket No. 09-cv-277-bbc, dated May 4, 2009.
Report on the Filing or Determination of an Action Regarding a Patent or Trademark, in the matter *Illumina, Inc.* v. *Affymetrix, Inc.*, U.S. District Court for the Western District of Wisconsin, Docket No. 09-cv-277-bbc, dated May 5, 2009.
Answer to Amended Complaint, in the matter *Illumina, Inc.* v. *Affymetrix, Inc.*, U.S. District Court for the Western District of Wisconsin, Docket No. 09-cv-277-bbc, dated Jun. 9, 2009.
Affymetrix, Inc's Motion to Transfer Venue, in the matter *Illumina, Inc.* v. *Affymetrix, Inc.*, U.S. District Court for the Western District of Wisconsin, Docket No. 09-cv-277-bbc, dated Jun. 9, 2009.
Memorandum of Defendant Affymetrix Inc. in Support of its Motion to Transfer Venue, in the matter *Illumina, Inc.* v. *Affymetrix, Inc.*, U.S. District Court for the Western District of Wisconsin, Docket No. 09-cv-277-bbc, dated Jun. 9, 2009.
Declaration of Stephen P.A. Fodor in Support of Affymetrix's Motion to Transfer Venue, in the matter *Illumina, Inc.* v. *Affymetrix, Inc.*, U.S. District Court for the Western District of Wisconsin, Docket No. 09-cv-277-bbc, dated Jun. 9, 2009.
Declaration of Roger J. Chin in Support of Affymetrix's Motion to Transfer Venue, in the matter *Illumina, Inc.* v. *Affymetrix, Inc.*, U.S. District Court for the Western District of Wisconsin, Docket No. 09-cv-277-bbc, dated Jun. 9, 2009.
Illumina's Answer to Defendant Affymetrix's Counterclaim, in the matter *Illumina, Inc.* v. *Affymetrix, Inc.*, U.S. District Court for the Western District of Wisconsin, Docket No. 09-cv-277-bbc, dated Jun. 29, 2009.
Illumina's Opposition to Affymetrix Inc's Motion to Transfer Venus, in the matter *Illumina, Inc.* v. *Affymetrix, Inc.*, U.S. District Court for the Western District of Wisconsin, Docket No. 09-cv-277-bbc, dated Jun. 30, 2009.
Declaration of Christian G. Cabou, in the matter *Illumina, Inc.* v. *Affymetrix, Inc.*, U.S. District Court for the Western District of Wisconsin, Docket No. 09-cv-277-bbc, dated Jun. 30, 2009.
Declaration of John Murphy, in the matter *Illumina, Inc.* v. *Affymetrix, Inc.*, U.S. District Court for the Western District of Wisconsin, Docket No. 09-cv-277-bbc, dated Jun. 30, 2009.
Declaration of John Izzo, in the matter *Illumina, Inc.* v. *Affymetrix, Inc.*, U.S. District Court for the Western District of Wisconsin, Docket No. 09-cv-277-bbc, dated Jun. 30, 2009.
Declaration of Robert A. Lawler, in the matter *Illumina, Inc.* v. *Affymetrix, Inc.*, U.S. District Court for the Western District of Wisconsin, Docket No. 09-cv-277-bbc, dated Jun. 30, 2009.

Joint Preliminary Pretrial Report, in the matter *Illumina, Inc.* v. *Affymetrix, Inc.*, U.S. District Court for the Western District of Wisconsin, Docket No. 09-cv-277-bbc, dated Jul. 1, 2009.
Reply Memorandum of Defendant Affymetrix, Inc. in Support of its Motion to Transfer Venue, in the matter *Illumina, Inc.* v. *Affymetrix, Inc.*, U.S. District Court for the Western District of Wisconsin, Docket No. 09-cv-277-bbc, dated Jul. 9, 2009.
Supplemental Declaration of Roger J. Chin in Support of Affymentrix's Motion to Transfer Venue, in the matter *Illumina, Inc.* v. *Affymetrix, Inc.*, U.S. District Court for the Western District of Wisconsin, Docket No. 09-cv-277-bbc, dated Jul. 9, 2009.
Preliminary Pretrial Conference Order, in the matter *Illumina, Inc.* v. *Affymetrix, Inc.*, U.S. District Court for the Western District of Wisconsin, Docket No. 09-cv-277-bbc, dated Jul. 10, 2009.
Affymetrix, Inc's Motion for Protective Order, in the matter *Illumina, Inc.* v. *Affymetrix, Inc.*, U.S. District Court for the Western District of Wisconsin, Docket No. 09-cv-277-bbc, dated Jul. 22, 2009.
Proposed Order Granting Motion for Protective Order, in the matter *Illumina, Inc.* v. *Affymetrix, Inc.*, U.S. District Court for the Western District of Wisconsin, Docket No. 09-cv-277-bbc, dated Jul. 22, 2009.
Memorandum of Deffendant Affymetrix Inc. in Support of its Motion for Protective Order, in the matter *Illumina, Inc.* v. *Affymetrix, Inc.*, U.S. District Court for the Western District of Wisconsin, Docket No. 09-cv-277-bbc, dated Jul. 22, 2009.
Reply Memorandum of Defendant Affymetrix Inc. in Support of its Motion for Protective Order, in the matter *Illumina, Inc.* v. *Affymetrix, Inc.*, U.S. District Court for the Western District of Wisconsin, Docket No. 09-cv-277-bbc, dated Jul. 31, 2009.
Answer to Second Amended Complaint, in the matter *Illumina, Inc.* v. *Affymetrix, Inc.*, U.S. District Court for the Western District of Wisconsin, Docket No. 09-cv-277-bbc, dated Aug. 28, 2009.
Illumina Inc's Answer to Defendant Affymetrix Inc's Counterclaim, in the matter *Illumina, Inc.* v. *Affymetrix, Inc.*, U.S. District Court for the Western District of Wisconsin, Docket No. 09-cv-277-bbc, dated Sep. 14, 2009.
Order Granting Motion for Protective Order Regardin RFAs, in the matter *Illumina, Inc.* v. *Affymetrix, Inc.*, U.S. District Court for the Western District of Wisconsin, Docket No. 09-cv-277-bbc, dated Sep. 16, 2009.
Opinion and Order Regarding Request for Transfer of Venue, in the matter *Illumina, Inc.* v. *Affymetrix, Inc.*, U.S. District Court for the Western District of Wisconsin, Docket No. 09-cv-277-bbc, dated Sep. 21, 2009.
Complaint for Patent Infringement, in the matter *Illumina, Inc.* v. *Affymetrix, Inc.*, U.S. District Court for the Western District of Wisconsin, Docket No. 09-cv-665-bbc, dated Nov. 3, 2009.
Exhibit A in Complaint for Patent Infringement, in the matter *Illumina, Inc.* v. *Affymetrix, Inc.*, U.S. District Court for the Western District of Wisconsin, Docket No. 09-cv-665-bbc, dated Nov. 3, 2009.
Civil Cover Sheet in Complaint for Patent Infringement, in the matter *Illumina, Inc.* v. *Affymetrix, Inc.*, U.S. District Court for the Western District of Wisconsin, Docket No. 09-cv-665-bbc, dated Nov. 3, 2009.
Summons in a Civil Action, in the matter *Illumina, Inc.* v. *Affymetrix, Inc.*, U.S. District Court for the Western District of Wisconsin, Docket No. 09-cv-665-bbc, dated Nov. 3, 2009.
Report on the Filing or Determination of an Action Regarding a Patent or Trademark, in the matter *Illumina, Inc.* v. *Affymetrix, Inc.*, U.S. District Court for the Western District of Wisconsin, Docket No. 09-cv-665-bbc, dated Nov. 3, 2009.
Illumina Inc's Disclosure of Corporate Affiliations and Financial Interest, in the matter *Illumina, Inc.* v. *Affymetrix, Inc.*, U.S. District Court for the Western District of Wisconsin, Docket No. 09-cv-665-bbc, dated Nov. 3, 2009.
Report on the Filing or Determination of an Action Regarding a Patent or Trademark Transmitted by Clerk, in the matter *Illumina, Inc.* v. *Affymetrix, Inc.*, U.S. District Court for the Western District of Wisconsin, Docket No. 09-cv-665-bbc, dated Nov. 3, 2009.

(56) References Cited

OTHER PUBLICATIONS

Summons in a Civil Action Transmitted by Clerk, in the matter *Illumina, Inc.* v. *Affymetrix, Inc.*, U.S. District Court for the Western District of Wisconsin, Docket No. 09-cv-665-bbc, dated Nov. 3, 2009.
Joint Motion for Consolidation, Continuance of Claim Constructions, and a Preliminary Pretrial Conference, in the matter *Illumina, Inc.* v. *Affymetrix, Inc.*, U.S. District Court for the Western District of Wisconsin, Docket No. 09-cv-277-bbc, dated Nov. 10, 2009.
Stipulated Protective Order, in the matter *Illumina, Inc.* v. *Affymetrix, Inc.*, U.S. District Court for the Western District of Wisconsin, Docket No. 09-cv-277-bbc, dated Nov. 10, 2009.
Proof of Service Regarding '020 Complaint, in the matter *Illumina, Inc.* v. *Affymetrix, Inc.*, U.S. District Court for the Western District of Wisconsin, Docket No. 09-cv-665-bbc, dated Nov. 24, 2009.
Affymetrix Answer to Complaint, in the matter *Illumina, Inc.* v. *Affymetrix, Inc.*, U.S. District Court for the Western District of Wisconsin, Docket No. 09-cv-665-bbc, dated Nov. 24, 2009.
Joint Preliminary Pretrial Report, in the matter *Illumina, Inc.* v. *Affymetrix, Inc.*, U.S. District Court for the Western District of Wisconsin, Docket No. 09-cv-277-bbc, dated Dec. 7, 2009.
Preliminary Pretrial Conference Order, in the matter *Illumina, Inc.* v. *Affymetrix, Inc.*, U.S. District Court for the Western District of Wisconsin, Docket No. 09-cv-277-bbc, dated Dec. 11, 2009.
Illumina Inc's Answer to Defendant Affymetrix Inc's Counterclaim, in the matter *Illumina, Inc.* v. *Affymetrix, Inc.*, U.S. District Court for the Western District of Wisconsin, Docket No. 09-cv-665-bbc, dated Dec. 14, 2009.
Amended Consolidated Complaint for Patent Infringement, in the matter *Illumina, Inc.* v. *Affymetrix, Inc.*, U.S. District Court for the Western District of Wisconsin, Docket No. 09-cv-277-bbc, dated Dec. 17, 2009.
Exhibit A to Amended Consolidated Complaint for Patent Infringement, in the matter *Illumina, Inc.* v. *Affymetrix, Inc.*, U.S. District Court for the Western District of Wisconsin, Docket No. 09-cv-277-bbc, dated Dec. 17, 2009.
Exhibit B to Amended Consolidated Complaint for Patent Infringement, in the matter *Illumina, Inc.* v. *Affymetrix, Inc.*, U.S. District Court for the Western District of Wisconsin, Docket No. 09-cv-277-bbc, dated Dec. 17, 2009.
Affymetrix Answer to Amended Consolidated Complaint, in the matter *Illumina, Inc.* v. *Affymetrix, Inc.*, U.S. District Court for the Western District of Wisconsin, Docket No. 09-cv-277-bbc, dated Dec. 31, 2009.
Illumina Inc's Answer to Defendant Affymetrix Inc's Counterclaim, in the matter *Illumina, Inc.* v. *Affymetrix, Inc.*, U.S. District Court for the Western District of Wisconsin, Docket No. 09-cv-277-bbc, dated Jan. 14, 2010.
Order Denying Mandamus to Transfer Venue, in the matter *Illumina, Inc.* v. *Affymetrix, Inc.*, U.S. District Court for the Western District of Wisconsin, Docket No. 09-cv-277-bbc, dated Apr. 16, 2010.
Declaration of Andrea M. Toldt in Support of Claim Construction and Exhibits A-E, in the matter *Illumina, Inc.* v. *Affymetrix, Inc.*, U.S. District Court for the Western District of Wisconsin, Docket No. 09-cv-277-bbc, dated Apr. 30, 2010.
Exhibits F-N filed with Declaration of Andrea M. Toldt, in the matter *Illumina, Inc.* v. *Affymetrix, Inc.*, U.S. District Court for the Western District of Wisconsin, Docket No. 09-cv-277-bbc, dated Apr. 30, 2010.
Motion of Defendant Affymetrix, Inc. Requesting Claim Construction and Memorandum in Support, in the matter *Illumina, Inc.* v. *Affymetrix, Inc.*, U.S. District Court for the Western District of Wisconsin, Docket No. 09-cv-277-bbc, dated Apr. 30, 2010.
Declaration of Roger J. Chin in Support of Affymetrix's Motion Requesting Claim Construction and Exhibits A-F, in the matter *Illumina, Inc.* v. *Affymetrix, Inc.*, U.S. District Court for the Western District of Wisconsin, Docket No. 09-cv-277-bbc, dated Apr. 30, 2010.
Exhibits G-T filed with Declaration of Roger J. Chin in Support of Affymetrix's Motion Requesting Claim Construction, in the matter *Illumina, Inc.* v. *Affymetrix, Inc.*, U.S. District Court for the Western District of Wisconsin, Docket No. 09-cv-277-bbc, dated Apr. 30, 2010.
Illumina Inc's Motion Requesting Claim Construction and Hearing, in the matter *Illumina, Inc.* v. *Affymetrix, Inc.*, U.S. District Court for the Western District of Wisconsin, Docket No. 09-cv-277-bbc, dated Apr. 30, 2010.
Illumina Inc's Opening Claim Construction Brief, in the matter *Illumina, Inc.* v. *Affymetrix, Inc.*, U.S. District Court for the Western District of Wisconsin, Docket No. 09-cv-277-bbc, dated Apr. 30, 2010.
Order Granting Motion for Hearing and Specifying Which Terms to be Construed, in the matter *Illumina, Inc.* v. *Affymetrix, Inc.*, U.S. District Court for the Western District of Wisconsin, Docket No. 09-cv-277-bbc, dated May 7, 2010.
Illumina Inc's Responsive Claim Construction Brief and Certificate of Service, in the matter *Illumina, Inc.* v. *Affymetrix, Inc.*, U.S. District Court for the Western District of Wisconsin, Docket No. 09-cv-277- bbc, dated May 21, 2010.
Affymetrix Inc's Responsive Claim Construction Brief and Certificate of Service, in the matter *Illumina, Inc.* v. *Affymetrix, Inc.*, U.S. District Court for the Western District of Wisconsin, Docket No. 09-cv-277- bbc, dated May 21, 2010.
Declaration of Andrea M. Toldt and Exhibits 1-6, in the matter *Illumina, Inc.* v. *Affymetrix, Inc.*, U.S. District Court for the Western District of Wisconsin, Docket No. 09-cv-277-bbc, dated May 21, 2010.
Stenographic Transcript of Claims Construction Hearing Held Before Judge Barbara B. Crabb, in the matter *Illumina, Inc.* v. *Affymetrix, Inc.*, U.S. District Court for the Western District of Wisconsin, Docket No. 09-cv-277-bbc, dated Jun. 14, 2010.
Order Construing Claim Terms, in the matter *Illumina, Inc.* v. *Affymetrix, Inc.*, U.S. District Court for the Western District of Wisconsin, Docket No. 09-cv-277-bbc, dated Jul. 14, 2010.
Motion of Defendant Affymetrix Inc. for Leave to Amend, Filed Under Seal in the matter *Illumina, Inc.* v. *Affymetrix, Inc.*, U.S. District Court for the Western District of Wisconsin, Docket No. 09-cv-277-bbc, dated Jul. 20, 2010.
Memorandum of Defendant Affymetrix Inc. in Support f Motion for Leave to Amend, Filed Under Seal in the matter *Illumina, Inc.* v. *Affymetrix, Inc.*, U.S. District Court for the Western District of Wisconsin, Docket No. 09-cv-277-bbc, dated Jul. 20, 2010.
Declaration of Roger J. Chin in Support of Affymetrix's Motion for Leave to Amend, Filed Under Seal, in the matter *Illumina, Inc.* v. *Affymetrix, Inc.*, U.S. District Court for the Western District of Wisconsin, Docket No. 09-cv-277-bbc, dated Jul. 20, 2010.
Illumina's Motion to File Under Seal, in the matter *Illumina, Inc.* v. *Affymetrix, Inc.*, U.S. District Court for the Western District of Wisconsin, Docket No. 09-cv-277-bbc, dated Jul. 27, 2010.
Illumina's Opposition to Affymetrix's Motion for Leave to Amend, Filed Under Seal in the matter *Illumina, Inc.* v. *Affymetrix, Inc.*, U.S. District Court for the Western District of Wisconsin, Docket No. 09-cv-277-bbc, dated Jul. 27, 2010.
Certificate of Service, in the matter *Illumina, Inc.* v. *Affymetrix, Inc.*, U.S. District Court for the Western District of Wisconsin, Docket No. 09-cv-277-bbc, dated Jul. 27, 2010.
Exhibit D in Support of Motion to Amend, in the matter *Illumina, Inc.* v. *Affymetrix, Inc.*, U.S. District Court for the Western District of Wisconsin, Docket No. 09-cv-277-bbc, dated Jul. 27, 2010.
Exhibit E in Support of Motion to Amend, in the matter *Illumina, Inc.* v. *Affymetrix, Inc.*, U.S. District Court for the Western District of Wisconsin, Docket No. 09-cv-277-bbc, dated Jul. 27, 2010.
Stipulation and Proposed Order, in the matter *Illumina, Inc.* v. *Affymetrix, Inc.*, U.S. District Court for the Western District of Wisconsin, Docket No. 09-cv-277-bbc, dated Aug. 2, 2010.
Order Granting Affymetrix's Motion to Amend, in the matter *Illumina, Inc.* v. *Affymetrix, Inc.*, U.S. District Court for the Western District of Wisconsin, Docket No. 09-cv-277-bbc, dated Aug. 27, 2010.
Certificate of Service, in the matter *Illumina, Inc.* v. *Affymetrix, Inc.*, U.S. District Court for the Western District of Wisconsin, Docket No. 09-cv-277-bbc, dated Aug. 30, 2010.

(56) References Cited

OTHER PUBLICATIONS

Illumina's Motion to File Under Seal, in the matter *Illumina, Inc.* v. *Affymetrix, Inc.*, U.S. District Court for the Western District of Wisconsin, Docket No. 09-cv-277-bbc, dated Aug. 30, 2010.
Order Denying Illumina's Motion for Reconsideration, in the matter *Illumina, Inc.* v. *Affymetrix, Inc.*, U.S. District Court for the Western District of Wisconsin, Docket No. 09-cv-277-bbc, dated Sep. 2, 2010.
Affymetrix, Inc's Motion to Extend Deposition of Milan Mrksich, in the matter *Illumina, Inc.* v. *Affymetrix, Inc.*, U.S. District Court for the Western District of Wisconsin, Docket No. 09-cv-277-bbc, dated Sep. 3, 2010.
Memorandum of Defendant Affymetrix, Inc. in Support of Motion to Extend Deposition of Milan Mrksich, in the matter *Illumina, Inc.* v. *Affymetrix, Inc.*, U.S. District Court for the Western District of Wisconsin, Docket No. 09-cv-277-bbc, dated Sep. 3, 2010.
Illumina's Motion to File Under Seal, in the matter *Illumina, Inc.* v. *Affymetrix, Inc.*, U.S. District Court for the Western District of Wisconsin, Docket No. 09-cv-277-bbc, dated Sep. 10, 2010.
Illumina's Brief in Opposition to Affymetrix's Motion to Extend Deposition of Dr. Milan Mrksich, in the matter *Illumina, Inc.* v. *Affymetrix, Inc.*, U.S. District Court for the Western District of Wisconsin, Docket No. 09-cv-277-bbc, dated Sep. 10, 2010.
Motion of Defendant Affymetrix, Inc. to Strike Expert Report of Cameron Weiffenbach, in the matter *Illumina, Inc.* v. *Affymetrix, Inc.*, U.S. District Court for the Western District of Wisconsin, Docket No. 09-cv-277-bbc, dated Sep. 14, 2010.
Declaration of Roger J. Chin Setting Forth Affymetrix's Expenses Incurred in Filing its Motion to Extend Deposition of Milan Mrksich, in the matter *Illumina, Inc.* v. *Affymetrix, Inc.*, U.S. District Court for the Western District of Wisconsin, Docket No. 09-cv-277-bbc, dated Sep. 16, 2010.
Motion of Defendant Affymetrix Inc. to Dismiss for Lack of Jurisdiction, in the matter *Illumina, Inc.* v. *Affymetrix, Inc.*, U.S. District Court for the Western District of Wisconsin, Docket No. 09-cv-277-bbc, dated Sep. 17, 2010.
Motion of Defendant Affymetrix Inc. for Summary Judgment of Noninfringement, in the matter *Illumina, Inc.* v. *Affymetrix, Inc.*, U.S. District Court for the Western District of Wisconsin, Docket No. 09-cv-277-bbc, dated Sep. 17, 2010.
Illumina's Motion to File Under Seal, in the matter *Illumina, Inc.* v. *Affymetrix, Inc.*, U.S. District Court for the Western District of Wisconsin, Docket No. 09-cv-277-bbc, dated Sep. 17, 2010.
Illumina's Motion for Partial Summary Judgment, in the matter *Illumina, Inc.* v. *Affymetrix, Inc.*, U.S. District Court for the Western District of Wisconsin, Docket No. 09-cv-277-bbc, dated Sep. 17, 2010.
Exhibits A-C filed with Declaration of Toldt, in the matter *Illumina, Inc.* v. *Affymetrix, Inc.*, U.S. District Court for the Western District of Wisconsin, Docket No. 09-cv-277-bbc, dated Sep. 17, 2010.
Exhibits D-F filed with Declaration of Toldt, in the matter *Illumina, Inc.* v. *Affymetrix, Inc.*, U.S. District Court for the Western District of Wisconsin, Docket No. 09-cv-277-bbc, dated Sep. 17, 2010.
Exhibits H-J filed with Declaration of Toldt, in the matter *Illumina, Inc.* v. *Affymetrix, Inc.*, U.S. District Court for the Western District of Wisconsin, Docket No. 09-cv-277-bbc, dated Sep. 17, 2010.
Exhibits L, N and O filed with Declaration of Toldt, in the matter *Illumina, Inc.* v. *Affymetrix, Inc.*, U.S. District Court for the Western District of Wisconsin, Docket No. 09-cv-277-bbc, dated Sep. 17, 2010.
Expert Report and Declaration of Dr. Milan Mrksich on Infringment, in the matter *Illumina, Inc.* v. *Affymetrix, Inc.*, U.S. District Court for the Western District of Wisconsin, Docket No. 09-cv-277-bbc, dated Sep. 17, 2010.
Brief in Support of Motion for Reconsideration of Order Granting Motion for Leave to Amend, in the matter *Illumina, Inc.* v. *Affymetrix, Inc.*, U.S. District Court for the Western District of Wisconsin, Docket No. 09-cv-277-bbc, dated Aug. 30, 3010.
Brief in Support of Illumina's Motion for Partial Summary Judgment, in the matter *Illumina, Inc.* v. *Affymetrix, Inc.*, U.S. District Court for the Western District of Wisconsin, Docket No. 09-cv-277-bbc, dated Sep. 17, 2010.
Illumina's Proposed Findings of Fact in Support of Illumina's Motion for Partial Summary Judgment, in the matter *Illumina, Inc.* v. *Affymetrix, Inc.*, U.S. District Court for the Western District of Wisconsin, Docket No. 09-cv-277-bbc, dated Sep. 17, 2010.
Notice of Electronic Filing of Standard Attachments for Judge Crabb Required to be Served on All Parties with Summons or Waiver of Service, in the matter *Illumina, Inc.* v. *Affymetrix, Inc.*, U.S. District Court for the Western District of Wisconsin, Docket No. 09-cv-665-bbc, dated Nov. 3, 2009.
Notice of Assigning of Case to Judge Barabara B. Crabb and Magistrate Judge Stephen L. Crocker, in the matter *Illumina, Inc.* v. *Affymetrix, Inc.*, U.S. District Court for the Western District of Wisconsin, Docket No. 09-cv-665-bbc, dated Nov. 3, 2009.
Order Accepting and Entering Stipulation for Protective Order, in the matter *Illumina, Inc.* v. *Affymetrix, Inc.*, U.S. District Court for the Western District of Wisconsin, Docket No. 09-cv-277-bbc, dated Nov. 10, 2009.
Notice of Set Pretrial Conference, in the matter *Illumina, Inc.* v. *Affymetrix, Inc.*, U.S. District Court for the Western District of Wisconsin, Docket Nos. 09-cv-277-bbc, 09-cv-665-bbc, dated Nov. 12, 2009.
Order Granting Joint Motion to Consolidated Case Nos. 09-cv-277-bbc and 09-cv-665-bbc, in the matter *Illumina, Inc.* v. *Affymetrix, Inc.*, U.S. District Court for the Western District of Wisconsin, Docket No. 09-cv-277-bbc, dated Nov. 12, 2009.
Order Granting Joint Motion to Consolidated Case Nos. 09-cv-277-bbc and 09-cv-665-bbc, in the matter *Illumina; Inc.* v. *Affymetrix, Inc.*, U.S. District Court for the Western District of Wisconsin, Docket No. 09-cv-665-bbc, dated Nov. 12, 2009.
Memorandum of Defendant Affymetrix, Inc. in Support of Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 17, 2010.
Defendant Affymetrix, Inc.'s Proposed Findings of Fact in Support of Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 17, 2010.
Memorandum of Defendant Affymetrix, Inc. in Support of Motion for Summary Judgment of Noninfringement, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 17, 2010.
Defendant Affymetrix, Inc.'s Proposed Findings of Fact in Support of Motion for Summary Judgment of Noninfringement, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 17, 2010.
Errata to Defendant Affymetrix, Inc's Proposed Findings of Fact in Support of Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 23, 2010.
Transcript of Video Deposition of John R. Stuelpnagel, D.V.M., in the matter *Illumina, Inc.* v. *Affymetrix, Inc.*, U.S. District Court for the Western District of Wisconsin, Docket Nos. 09-cv-277-bbc, 09-cv-665-bbc (Consolidated), dated Jul. 13, 2010.
Transcript of Video Deposition of Mark Chee, Ph.D., in the matter *Illumina, Inc.* v. *Affymetrix, Inc.*, U.S. District Court for the Western District of Wisconsin, Docket Nos. 09-cv-277-bbc, 09-cv-665-bbc (Consolidated), dated Jul. 23, 2010.
Expert Report of Kevin Struhl, Ph.D. and Certificate of Service, in the matter *Illumina, Inc.* v. *Affymetrix, Inc.*, U.S. District Court for the Western District of Wisconsin, Docket Nos. 09-cv-277-bbc, 09-cv-665-bbc (Consolidated), dated Aug. 2, 2010.
Defendant Affymetix, Inc's Opposition to Plaintiff's Motion for Reconsideration, in the matter *Illumina, Inc.* v. *Affymetrix, Inc.*, Filed

(56) References Cited

OTHER PUBLICATIONS

Under Seal (Redacted), U.S. District Court for the Western District of Wisconsin, Docket Nos. 09-cv-277-bbc, 09-cv-665-bbc (Consolidated), dated Aug. 31, 2010.
Expert Report and declaration of Dr. Milan Mrksich on Validity, in the matter *Illumina, Inc.* v. *Affymetrix, Inc.*, (Redacted) U.S. District Court for the Western District of Wisconsin, Docket Nos. 09-cv-277-bbc, 09-cv-665-bbc (Consolidated), dated Sep. 3, 2010.
Memorandum of Defendant Affymetix, Inc. in Support of Motion to Strike Expert Report of Cameron Weiffenbach, in the matter *Illumina, Inc.* v. *Affymetrix, Inc.*, (Redacted) U.S. District Court for the Western District of Wisconsin, Docket Nos. 09-cv-277-bbc, 09-cv-665-bbc (Consolidated), dated Sep. 14, 2010.
Illumina's Answer to Affymetrix's Counterclaim (Redacted), in the matter *Illumina, Inc.* v. *Affymetrix, Inc.*, U.S. District Court for the Western District of Wisconsin, Docket Nos. 09-cv-277-bbc, 09-cv-665- bbc (Consolidated), dated Sep. 17, 2010.
Declaration of Martin Goldberg in Support of Affymetrix's Motion for Summary Judgment of Noninfringement, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Sep. 17, 2010.
Illumina's Brief in Opposition to Affymetrix's Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Oct. 8, 2010.
Illumina's Proposed Findings of Fact in Support of Illumina's Brief in Opposition to Affymetrix's Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Oct. 8, 2010.
Declaration of Kimberly K. Dodd in opposition to Affymetrix's Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Oct. 8, 2010.
Illumina's Response to Defendant Affymetrix, Inc.'s Proposed Findings of Fact in Support of Motion to Dismiss for Lack of Jurisdiction, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Oct. 8, 2010.
Reply Brief in Support of Illumina's Motion for Partial Summary Judgment, in the matter *Illumina, Inc.* v. *Affymetrix, Inc.*, Filed Under Seal (Redacted), U.S. District Court for the Western District of Wisconsin, Docket Nos. 09-cv-277-bbc, 09-cv-665-bbc (Consolidated), dated Oct. 18, 2010.
Illumina's Response to Defendant Affymetrix's, Inc's Proposed Findings of Fact in Opposition to Plaintiff's Motion for Partial Summary Judgment, in the matter *Illumina, Inc.* v. *Affymetrix, Inc.*, Filed Under Seal, U.S. District Court for the Western District of Wisconsin, Docket Nos. 09-cv-277-bbc, 09-cv-665-bbc (Consolidated), dated Oct. 18, 2010.
Illumina's Reply to Affymetrix's Responses to Illumina's Proposed Findings of Fact in Support of Illumina's Motion for Partial Summary Judgment, in the matter *Illumina, Inc.* v. *Affymetrix, Inc.*, Filed Under Seal, U.S. District Court for the Western District of Wisconsin, Docket Nos. 09-cv-277-bbc, 09-cv-665-bbc (Consolidated), dated Oct. 18, 2010.
Order Requiring Additional Briefing Regarding Motion to Dismiss for Lack of Jurisdiction, in the matter *Illumina, Inc.* v. *Affymetrix, Inc.*, U.S. District Court for the Western District of Wisconsin, Docket Nos. 09-cv-277-bbc, 09-cv-665-bbc (Consolidated), dated Oct. 29, 2010.
Declaration of Gina A. Bibby in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit C to Declaration of Gina A. Bibby in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Declaration of Thomas T. Carmack in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit A to Declaration of Thomas T. Carmack in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit B to Declaration of Thomas T. Carmack in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit C to Declaration of Thomas T. Carmack in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit D to Declaration of Thomas T. Carmack in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Declaration of Kimberly K. Dodd in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit A to Declaration of Kimberly K. Dodd in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit B to Declaration of Kimberly K. Dodd in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.
Exhibit E to Declaration of Kimberly K. Dodd in Support of Illumina's Motion to Compel Production of Documetns Withheld by Gregory Kirk, in the matter *Illumina, Inc.* v. *Affymetrix, Inc.*, U.S. District Court Northern District of California San Francisco Division, Docket No. 10-mc-80226-CRB (Docket Nos. 09-cv-277-bbc, 09-cv-665-bbc (Consolidated Actions in the Western District of Wisconsin)), dated Nov. 2, 2010.

(56) References Cited

OTHER PUBLICATIONS

Supplemental Brief in Support of Affymetrix's Motion to Dismiss for Lack of Jurisdiction, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 8, 2010.

Declaration of Gregory Kirk, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 8, 2010.

Response to Court's Order of Oct. 29, 2010 Regarding Standing, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 8, 2010.

Illumina's Reply Regarding Court's Order of Oct. 29, 2010 Regarding Standing, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 10, 2010.

Supplemental Reply Brief in Support of Affymetrix's Motion to Dismiss for Lack of Jurisdiction, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 10, 2010.

Opinion and Order Regarding 256 Hearing, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Nov. 23, 2010.

Exhibit Regarding Order Regarding 256 Hearing, in the matter *Illumina, Inc. v. Affymetrix, Inc.*, U.S. District Court for the Western District of Wisconsin, Docket Nos. 09-cv-277-bbc, 09-cv-665-bbc (Consolidated), dated Mar. 9, 1998.

Letter dated Sep. 20, 2010 filed on behalf of Proprietor in connection with the Opposition of European Patent Application No. 05010428.0.

Letter dated Sep. 24, 2009 filed on behalf of Opponent in connection with the Appeal of an Opposition of European Patent EP 1141712.

Letter dated Oct. 2, 2009 and corresponding attachments filed on behalf of Proprietor in connection with the Appeal of an Opposition of European Patent EP 1141712.

Letter dated Apr. 9, 2010 and corresponding attachments filed on behalf of Proprietor in connection with the Appeal of an Opposition of European Patent EP 1141712.

Letter dated Apr. 19, 2010 and corresponding attachments filed on behalf of Opponent in connection with the Appeal of an Opposition of European Patent EP 1141712.

Minutes of the oral proceedings dated Nov. 25, 2008 in connection with the Opposition of European Patent EP 1141712.

Interlocutory decision in Opposition proceedings dated May 25, 2009 in connection with the Opposition of European Patent EP 1141712.

Datasheet Array, Retrieved from the internet URL: http//dictionary.reference.com/browse/array, printed Sep. 3, 2010.

Datasheet Plate, Retrieved from the internet URL: http//dictionary.reference.com/browse/plate, printed Sep. 3, 2010.

Minutes of Oral Proceedings, dated Dec. 28, 2011, in connection with the Opposition of European Patent EP 1593967.

Decision of Opposition Division, dated Dec. 29, 2011, in connection with the Opposition of European Patent EP 1593967.

Proprietor's Notice of Appeal against Decision from the Opposition Division, dated Mar. 6, 2012, in connection with the Opposition of European Patent EP 1593967.

U.S. Appl. No. 09/189,543, filed Nov. 10, 1998, Chee et al.

U.S. Appl. No. 09/606,369, filed Jun. 28, 2000, Stuelpnagel et al.

Abel, A., et al., "Fiber-optic evanescent wave biosensor for the detection of oligonucleotides," *Anal. Chem.* 68(17): 2905-2912, Sep. 1996.

Anonymous, "Fluorescent Microspheres," Tech. Note 19, Bang Laboratories, (Fishers, In) Feb. 1997.

Anonymous, "Microsphere Selection Guide," Bang Laboratories, (Fisher, In) Sep. 1998.

Barker et al., "Development and Cellular Applications of Fiber Optic Nitric Oxide Sensors based on a Gold-Adsorbed Fluorophore," *Analytical Chemistry*, 70: 4902-4906 (1998).

Bangs, L.B., "Immunological Applications of Microspheres," The Latex Course, Bangs Laboratories (Carmel, IN) Apr. 1996.

Barnard et al., "A Fibre-Optic Chemical Sensor with Discrete Sensing Sites," Nature, 353:338-340 (Sep. 1991).

Czarnik, "Illuminating the SNP Genomic Code," Modern Drug Discovery, 1(2):49-55 (1998).

Drmanac, R. et al., "Prospects for a Miniaturized, Simplified and Frugal Human Genome Project," Scientia Yugoslavica, 16(1-2):97-107 (1990).

Drmanac, R. et al., "Sequencing by Hybridization (SBH) with Oligonucleotide Probes as an Integral Approach for the Analysis of Complex Genomes," International Journal of Genome Research, 1(1):59-79 (1992).

Drmanac, R. et al., "Sequencing by Hybridization," Automated DNA Sequencing and Analysis, ed. M. Adams, C. Fields and J. Venter. (1994).

Drmanac, R. et al., "Sequencing by Oligonucleotide Hybridization: A Promising Framework in Decoding of the Genome Program," The First International Conference on Electrophoresis, Supercomputing and the Human Genome, Proceedings on Apr. 10-13, 1990 Conference at Florida State University. Ed. C. Cantor and H. Lim.

Ferguson et al., "A Fiber-Optic DNA Biosensor Microarray for the Analysis of Gene Expression," Nature Biotechnology, 14:1681-1684 (1996).

Fuh et al., "Single Fibre Optic Fluorescence pH Probe," Analyst, 112:1159-1163 (1987).

Guo et al., "Direct Fluorescence analysis of genetic polymorphisms by hybridization with oligonucleotide arrays on glass supports," *Nucleic Acids Research*, 1994, Oxford University Press, vol. 22, No. 24, pp. 5456-5465.

Healey et al., "Development of a Penicillin Biosensor Using a Single Optical Imaging Fiber," SPIE Proc. 2388:568-573 (1995).

Healey, et al. "Fiberoptic DNA Sensor Array Capable of Detecting Point Mutations." Analytical Biochemistry (1997), 251: 270-279.

Healey et al., "Improved Fiber-Optic Chemical Sensor for Penicillin," Anal. Chem. 67(24):4471-4476 (1995).

Hirschfeld et al., "Laser-Fiber-Optic 'Optrode' for Real Time In Vivo Blood Carbon Dioxide Level Monitoring," Journal of Lightwave Technology, LT-5(7):1027-1033 (1987).

Illumina Inc., "Emerging," Windhover's in Vivo, The Business and Medicine Report, 1-2 (1998).

Illumina Inc., Slides presented by Illumina at Cambridge Healthtech Institute's Implications of Human Genetic Variation—SNP's, Polymorphisms, Diseases & Treatment. Nov. 18-19, 1998, Waltham, Massachusetts.

Michael et al., "Fabrication of Micro- and Nanostructures Using Optical Imaging Fibers and Their Use as Chemical Sensors," Proc. $3^{rd}$ Intl. Symp., Microstructures and Microfabricated Systems, ed. P.J. Hesketh, et al., v. 97-5, Electrochem. Sock., 152-157 (Aug. 1997).

Michael et al., "Making Sensors out of Disarray: Optical Sensor Microarrays," Proc. SPIE, 3270:34-41 (1998).

Michael et al., "Randomly Ordered Addressable High-Density Optical Sensor Arrays," Anal. Chem. 70(7):1242-1248 (Apr. 1998).

Mignani et al., "In-Vivo Biomedical Monitoring by Fiber-Optic Systems," Journal of Lightwave Technology, 13(7)1396-1406 (1995).

Pantano et al., "Ordered Nanowell Arrays," Chem. Mater., 8(12):2832-2835 (1996).

Peterson et al., "Fiber-Optic Sensors for Biomedical Applications," Science, 12:123-127 (1984).

Peterson, J. et al., "Fiber Optic pH Probe for Physiological Use," Anal. Chem., 52:864-869 (1980).

Piunno et al., "Fiber-Optic DNA Sensor for Fluorometric Nucleic Acid Determination," Anal. Chem., 67:2635-2643 (1995).

Pope, E. "Fiber Optic Chemical Microsensors Employing Optically Active Silica Microspheres," SPIE, 2388:245-256 (1995).

Strachan et al., "A Rapid General Method for the Identification of PCR Products Using a Fibre-Optic Biosensor and its Application to the Detection of Listeria," Letters in Applied Microbiology, 21:5-9 (1995).

(56) References Cited

OTHER PUBLICATIONS

Venton et al., "Screening Combinatorial Libraries," Chemometrics and Intelligent Laboratory Systems, NL, Elsevier Science Publishers, Amsterdam, 48: 131-150 (1999).
Walt, D., "Fiber-Optic Sensors for Continuous Clinical Monitoring," Proc. IEEE, 80(6):903-911 (1992).
Walt, et al. "Fiber Optic Imaging Sensors." Accounts of Chemical Research (1998), 31: 267-278.
Zhou, et al, "Dispersion of nanospheres on large glass substrate by amorphous or polycrystalline silicon deposition for localized surface plasmon resonance" *J. Nanopart. Res.* (2009) 11: 2061-2069 and supporting information.
*DNA Microarrays: A Practical Approach*, ed. M. Schena, 1999, Oxford University Press Inc., New York, NY, Chapter 6.
Opponent's Supplemental Written Submission in Preparation of Oral Proceedings, dated Oct. 7, 2011, in connection with the Opposition of European Patent EP 1593967.
Declaration of Professor Tony Cass, dated Oct. 7, 2011, in connection with the Opposition of European Patent EP 1593967.
Declaration of Glenn McGall, dated Oct. 6, 2011, in connection with the Opposition of European Patent EP 1593967.
Lachenal, Gilbert, "Dispersive and Fourier transform near-infrared spectroscopy of polymeric materials" *Vibrational Spectroscopy* (1995) 9: 93-100.
"96 Well Plate Dimensions" down loaded from the internet at http://catalog2.corning.com, printed on Jul. 8, 2011.
Plaintiff-Appellant's Appeal Brief, in the matter, *Illumina, Inc.* v. *Affymetrix, Inc.*, U.S. Court of Appeals for the Federal Circuit, Docket Nos. 2011-1145, -1146, dated Mar. 3, 2011.
Defendant-Appellee's Appeal Brief, in the matter, *Illumina, Inc.* v. *Affymetrix, Inc.*, U.S. Court of Appeals for the Federal Circuit, Docket Nos. 2011-1145, -1146, dated Apr. 18, 2011.
Plaintiff-Appellant's Reply Appeal Brief, in the matter, *Illumina, Inc.* v. *Affymetrix, Inc.*, U.S. Court of Appeals for the Federal Circuit, Docket Nos. 2011-1145, -1146, dated May 5, 2011.
Judgment issued in the matter, *Illumina, Inc.* v. *Affymetrix, Inc.*, U.S. Court of Appeals for the Federal Circuit, Docket Nos. 2011-1145, -1146, dated Aug. 22, 2011.
Summons to Attend Oral Proceedings, dated Apr. 7, 2011, in connection with the Opposition of European Patent EP 1593967.
Opponent's Written Submission in Preparation of Oral Proceedings, dated Aug. 10, 2011, in connection with the Opposition of European Patent EP 1593967.
The home page from the website of Illumina, Inc. as that website existed on Oct. 23, 1999.
The technology page from the website of Illumina, Inc. as that website existed on Oct. 1, 1999.
The company profile page from the website of Illumina, Inc. as that website existed on Oct. 23, 1999.
An affidavit from the Office Manager at the Internet Archive, San Francisco, California, confirming public availability of the website and the pages Non Patent Literature Documents Nos. 10-12 listed on this PTO/SB/08 Equivalent, dated Jul. 29, 2011.
Illumina, Inc. press release regarding, PE Biosystems and Illumina Announce Strategic Collaboration to Develop and Commercialize High-Throughput DNA Array Systems, dated Nov. 9, 1999.
Michael, et al., "Randomly Ordered Addressable High-Density Optical Sensor Arrays" *Anal. Chem.* (1998) 70: 1242-1248.
Illumina, Inc. press release regarding, Illumina Raises $8.5 Million; Recruits Key Scientific Management Team; Establishes Scientific Advisory Board, dated Dec. 17, 1998.
Statement of Inventorship and right to grant filed in European Patent App. No. 05010428.0, which resulted in European Patent No. 1593967, dated May 10, 2005.
Assignment from Inventors to Illumina in U.S. Appl. No. 09/256,943, record at Reel: 009962, Frame: 0507, dated May 25, 1999.
Steven Auger's "Linkedin" profile, Aug. 10, 2011.
The history page from the website of Illumina, Inc. obtained Aug. 8, 2011.
Opponent's Written Submission in Preparation of Oral Proceedings, dated Sep. 8, 2011, in connection with the Opposition of European Patent EP 1593967.
Declaration of Professor Andre Sharon, dated Sep. 7, 2011, in connection with the Opposition of European Patent EP 1593967.
Declaration of Professor John David Sutherland, dated Sep. 8, 2011, in connection with the Opposition of European Patent EP 1593967.
*Pharmacogenetics—Bridging the Gap Between Basic Science and Clinical Application*, Published Nov. 1996, Edited and updated from the transcripts of the IBC conference, "Pharmacogenetics: Bridging the Gap between Basic Science and Clinical Application", held May 20-22, 1996, in Arlington, VA, Chapters 5.2 and 5.4.
Proprietor's Written Submission in Preparation of Oral Proceedings, dated Sep. 8, 2011, in connection with the Opposition of European Patent EP 1593967.
Johnston, Mark, "Gene chips: Array of hope for understanding gene regulation" *Current Biology* (1998) 8: R171-R174.
Approved Judgment, in the matter *KCI Licensing Inc. & Ors,* v. *Smith & Nephew plc. & Ors*, Royal Courts of Justice, Strand, London, WC2A 2LL, Case No. A3/2010/1929 & 1993, dated Nov. 18, 2010.
Complaint for Correction of Inventorship, in the matter *Affymetrix, Inc.* and *Gregory L. Kirk,* v. *Illumina, Inc.*, U.S. District Court for the Western District of Wisconsin, Docket No. 3:11-cv-00184, dated Mar. 14, 2011.
Certified Priority Document of U.S. Appl. No. 60/133,968, dated Feb. 16, 2000.
Certified Priority Document of U.S. Appl. No. 60/181,631, dated May 22, 2001.
Certified Priority Document of U.S. Appl. No. 09/256,943, dated Feb. 29, 2000.

\* cited by examiner

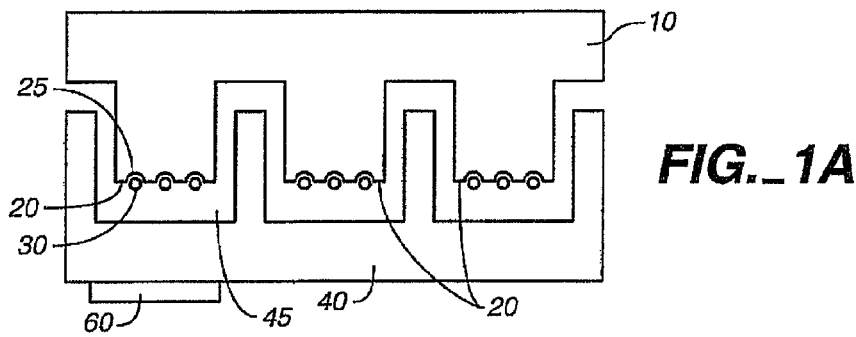
FIG._1A
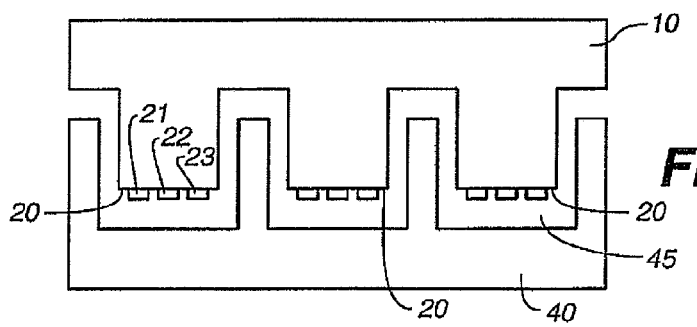
FIG._1B
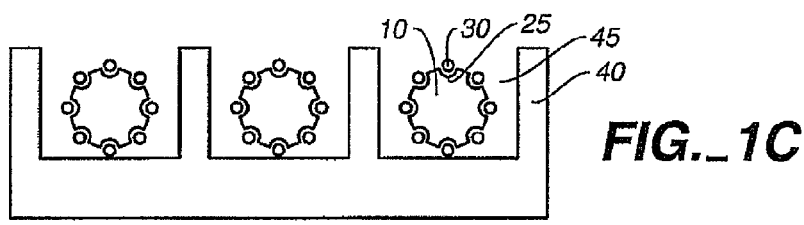
FIG._1C
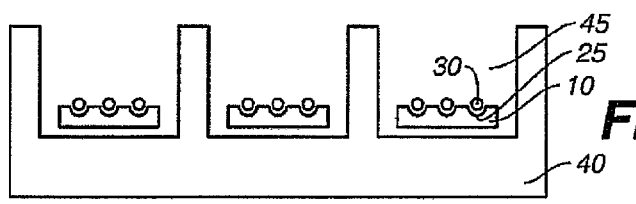
FIG._1D
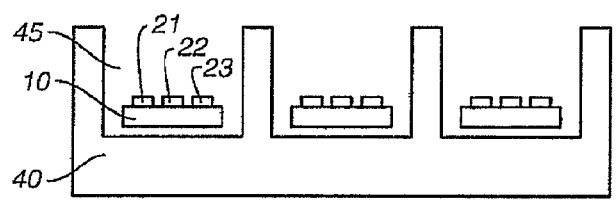
FIG._1E

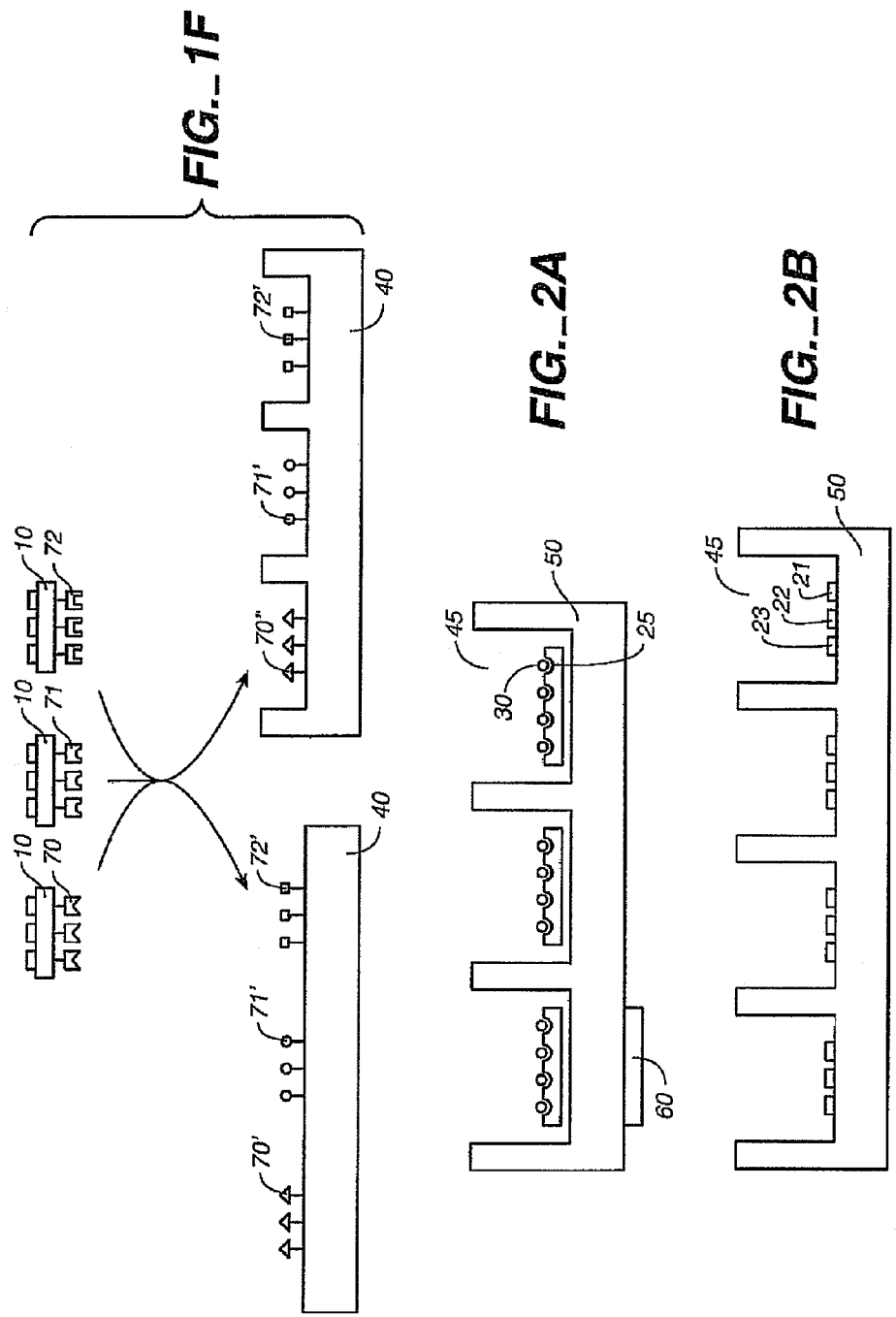

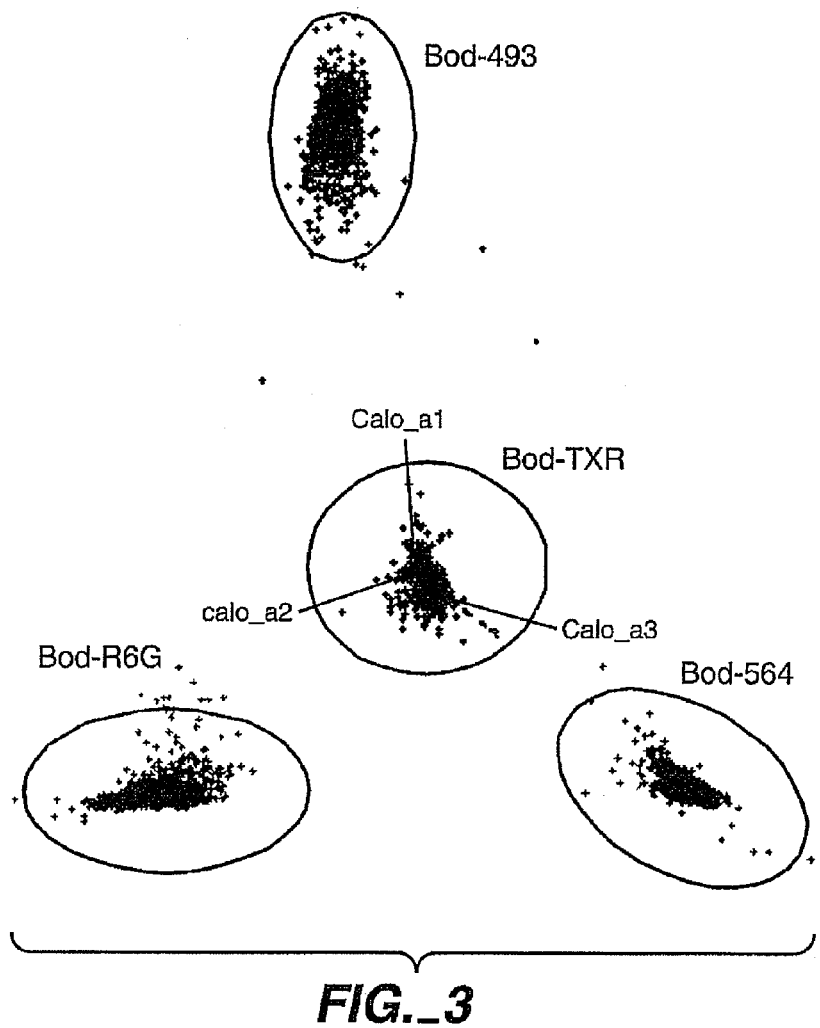
FIG._3

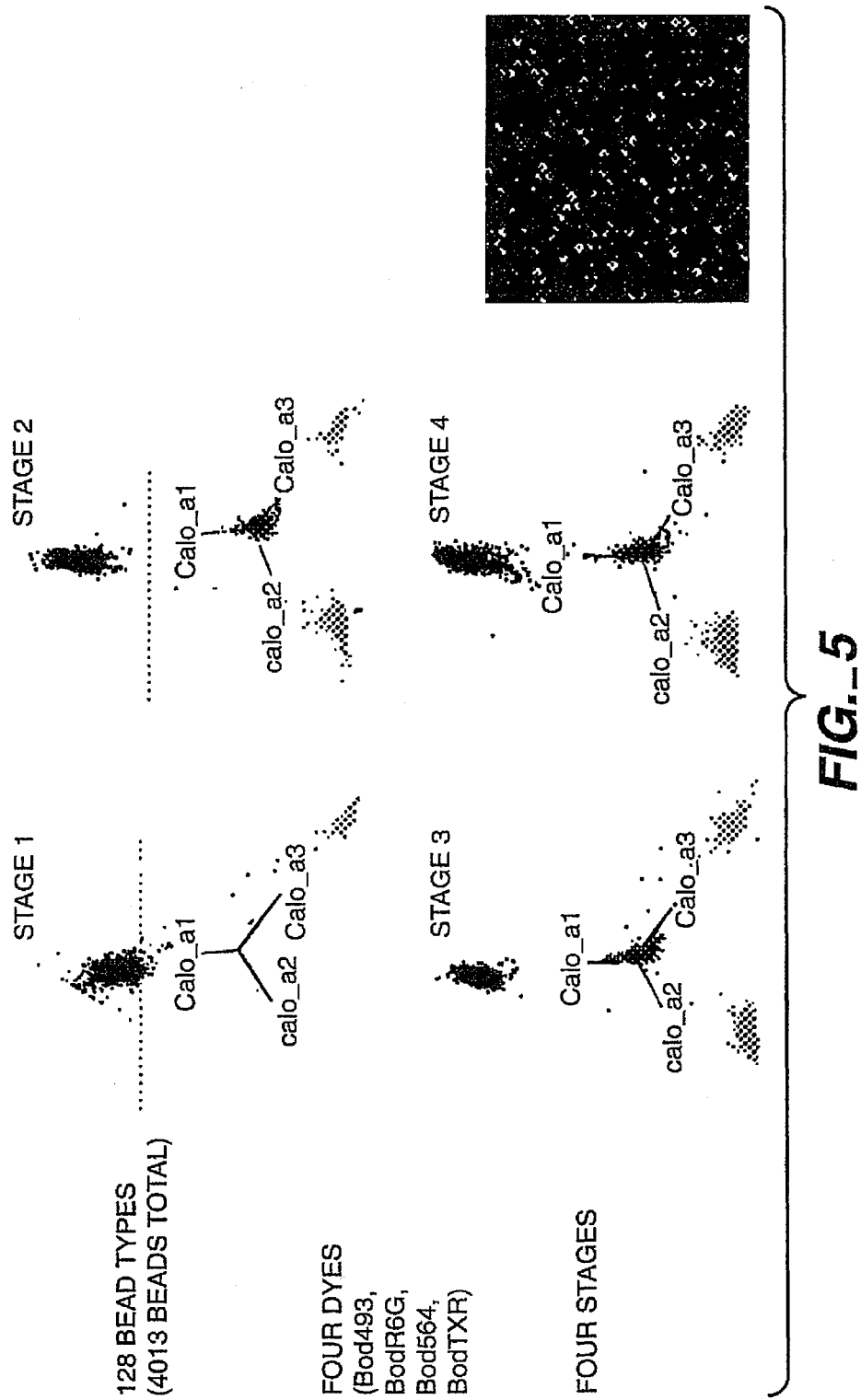
FIG._5

GREYSCALE DECODING
| Code | S1 | S2 | S3 |
|---|---|---|---|
| 1 | 100 | 100 | 100 |
| 2 | 100 | 100 | 40 |
| 3 | 100 | 100 | 10 |
| 4 | 100 | 40 | 100 |
| 5 | 100 | 40 | 40 |
| 6 | 100 | 40 | 10 |
| 7 | 100 | 10 | 100 |
| 8 | 100 | 10 | 40 |
| 9 | 100 | 10 | 10 |
| 10 | 40 | 100 | 100 |
| 11 | 40 | 100 | 40 |
| 12 | 40 | 100 | 10 |
| 13 | 40 | 40 | 100 |
| 14 | 40 | 40 | 40 |
| 15 | 40 | 40 | 10 |
| 16 | 40 | 10 | 100 |
| 17 | 40 | 10 | 40 |
| 18 | 40 | 10 | 10 |
| 19 | 10 | 100 | 100 |
| 20 | 10 | 100 | 40 |
| 21 | 10 | 100 | 10 |
| 22 | 10 | 40 | 100 |
| 23 | 10 | 40 | 40 |
| 24 | 10 | 40 | 10 |
| 25 | 10 | 10 | 100 |
| 26 | 10 | 10 | 40 |
| 27 | 10 | 10 | 10 |
FIG._6A
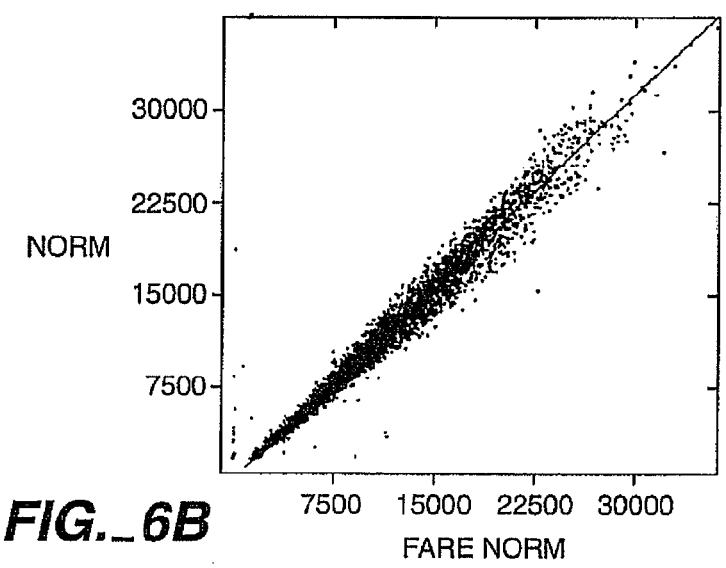
FIG._6B

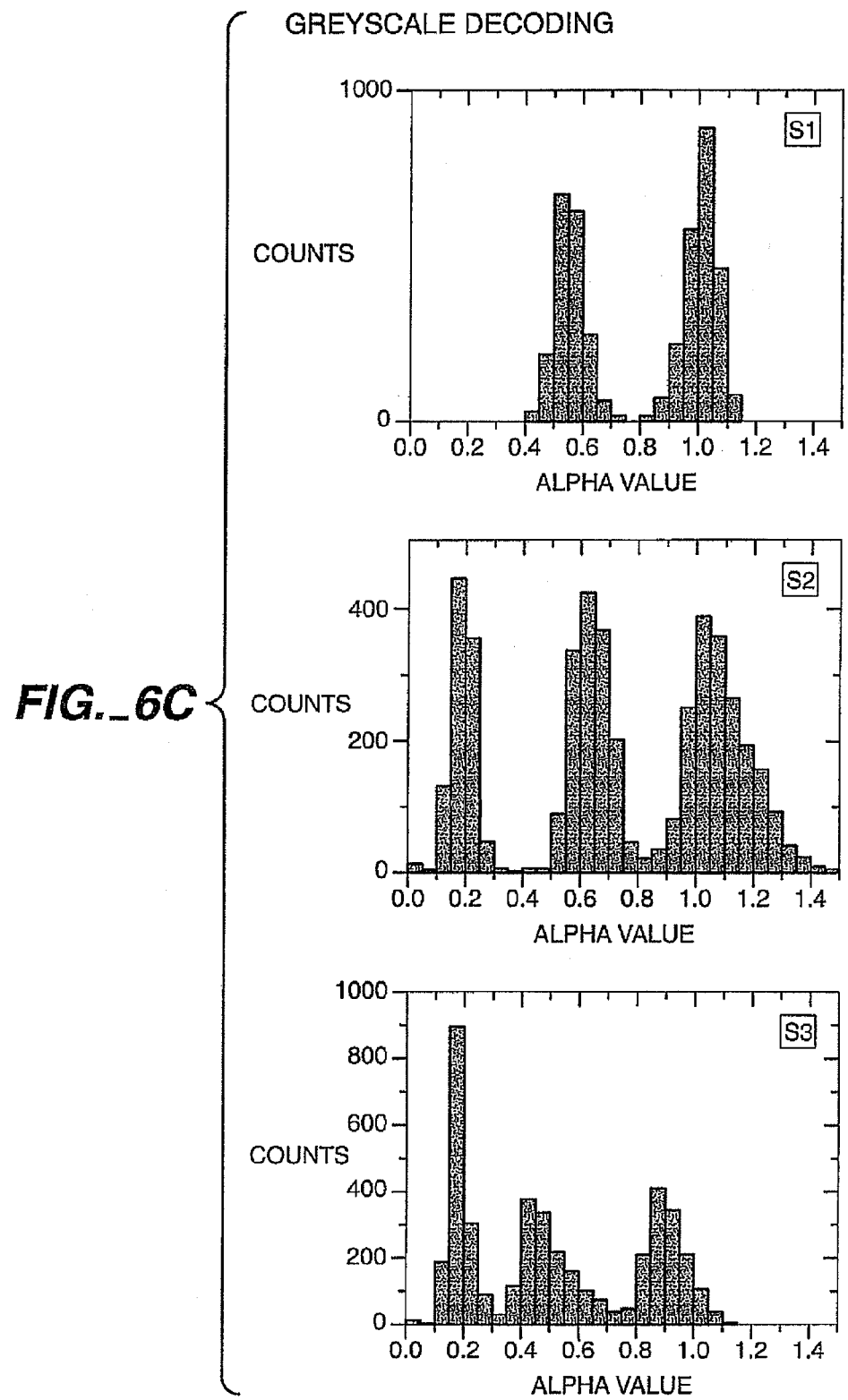
FIG._6C

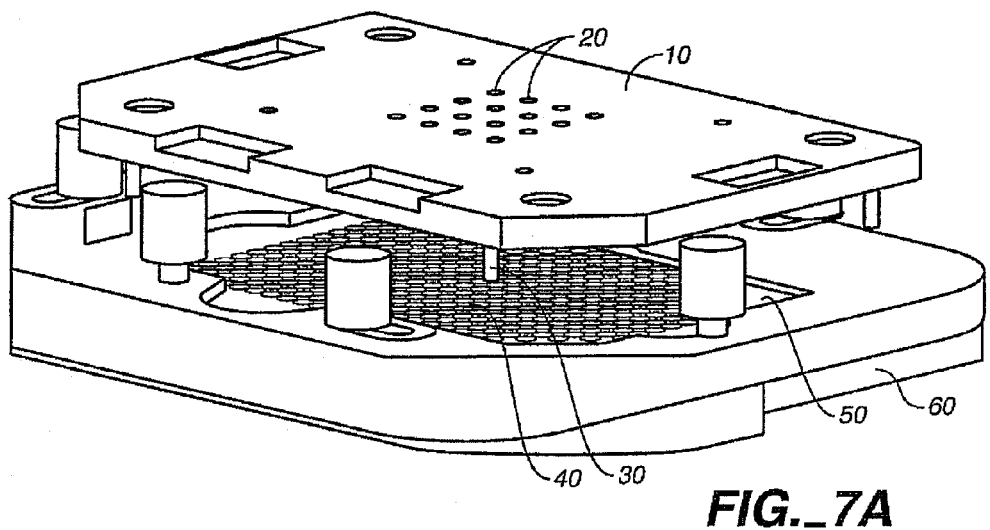
FIG._7A
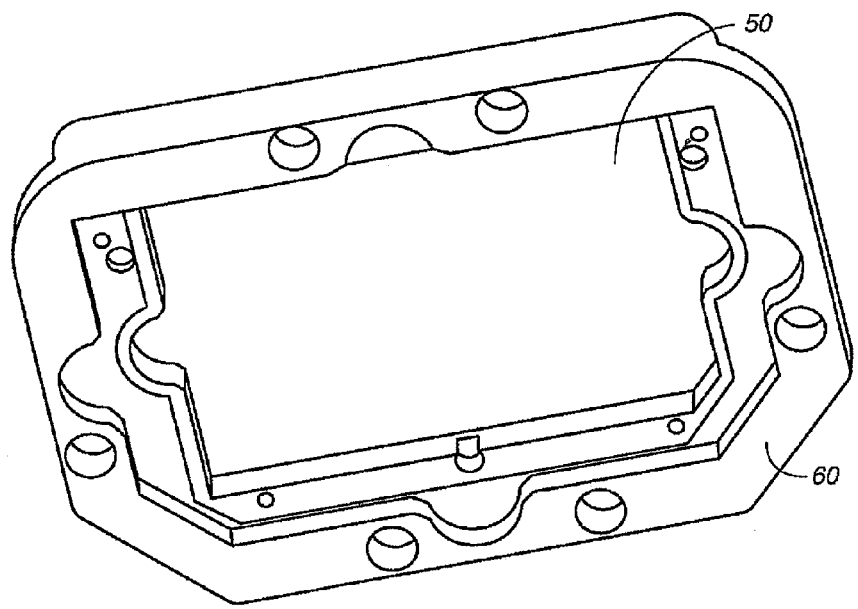
FIG._7B

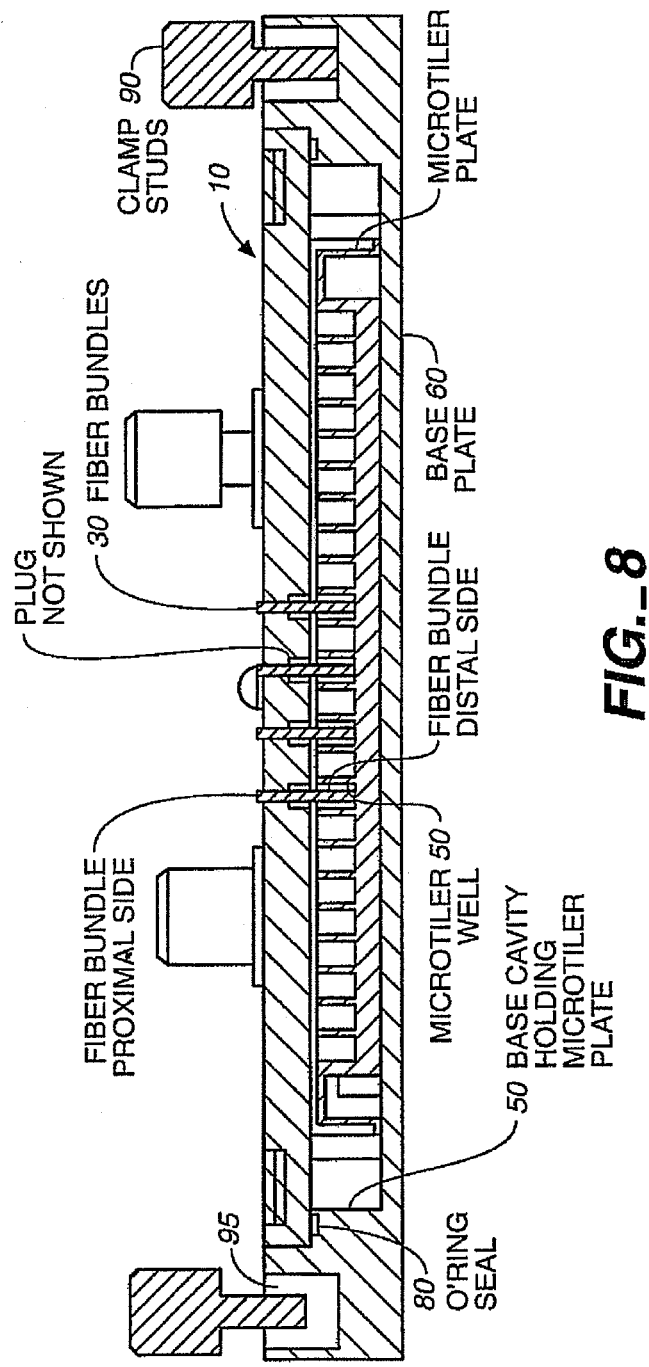
FIG._8

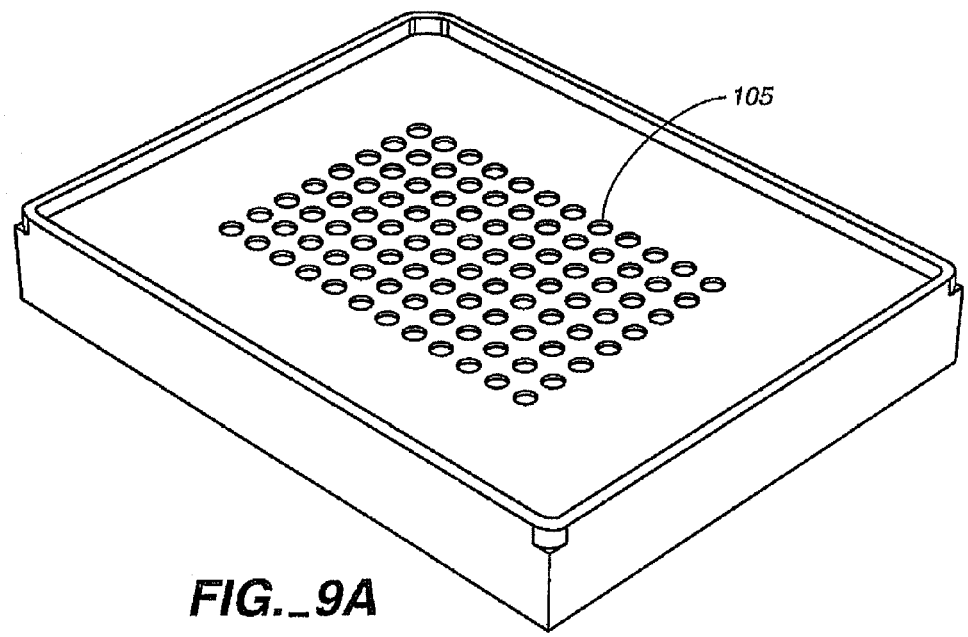
FIG._9A
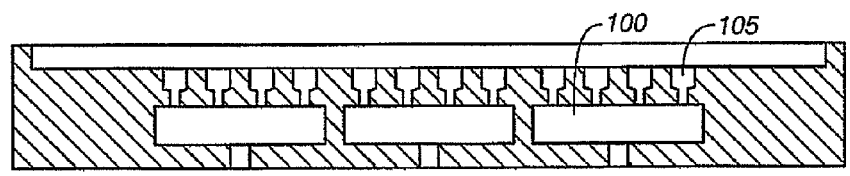
FIG._9B

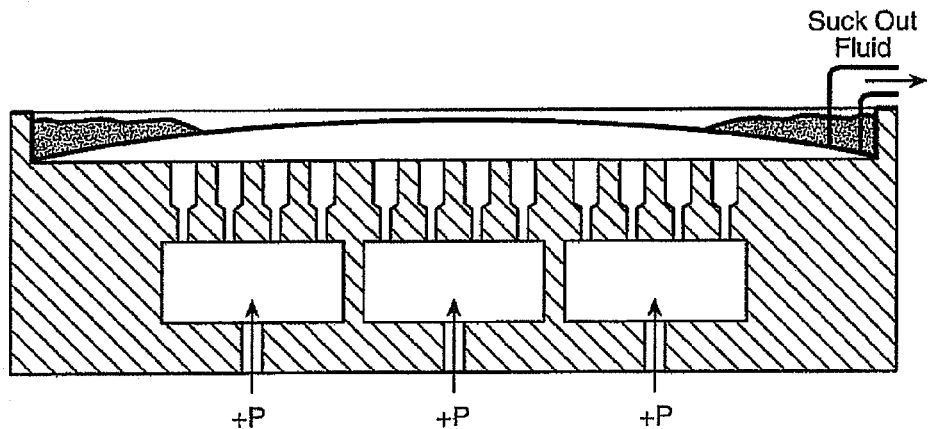
FIG._10A
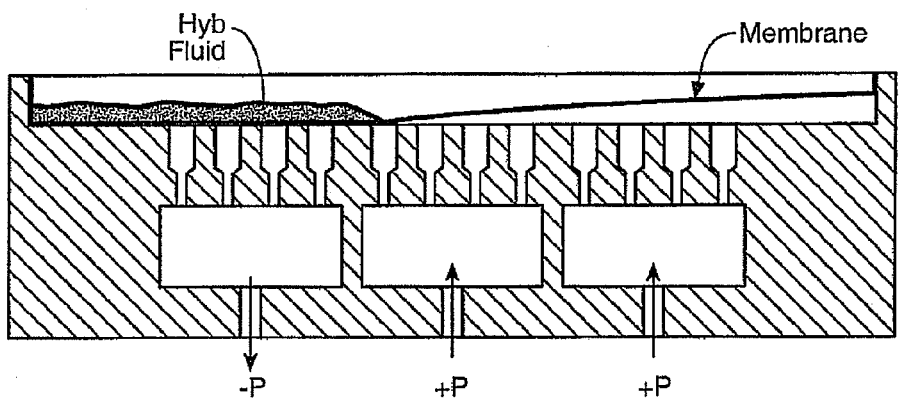
FIG._10B
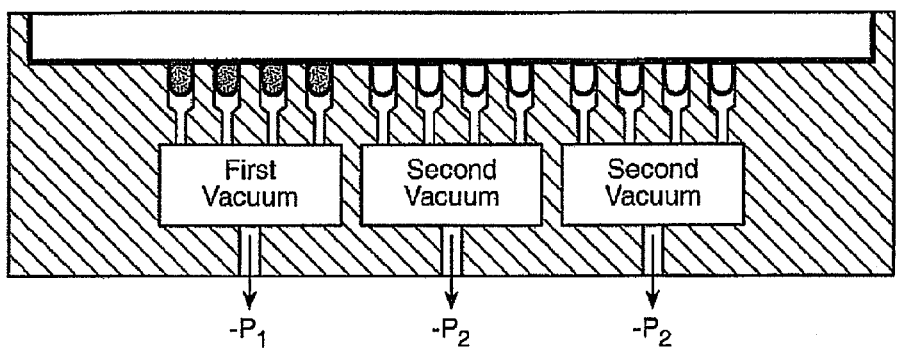
FIG._10C

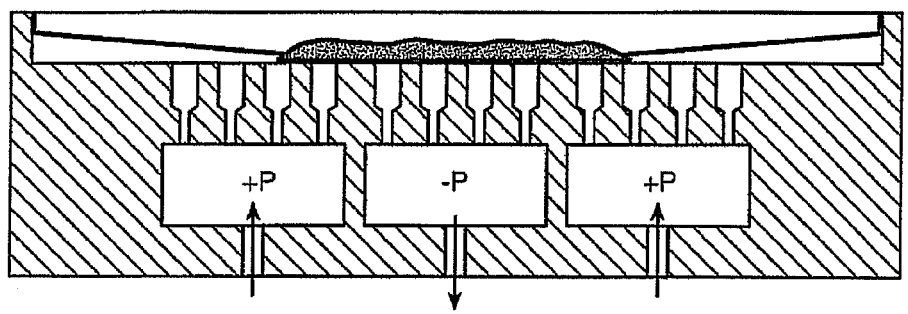
FIG._10D
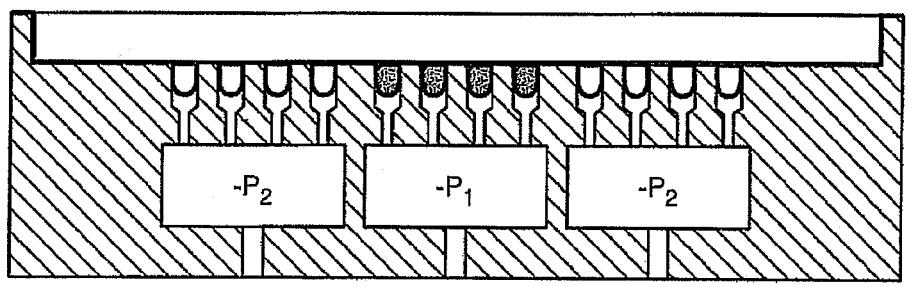
FIG._10E
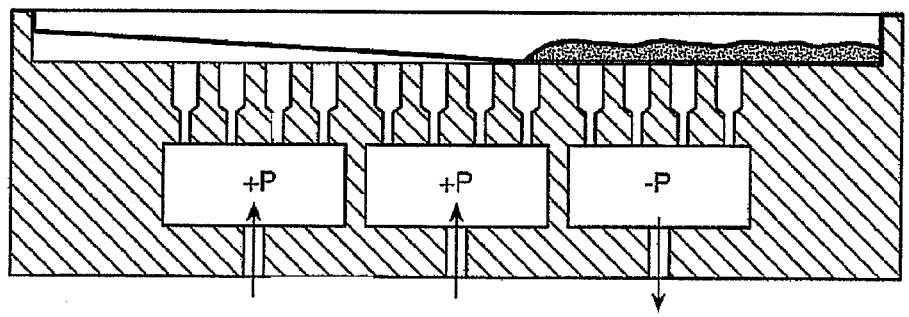
FIG._10F

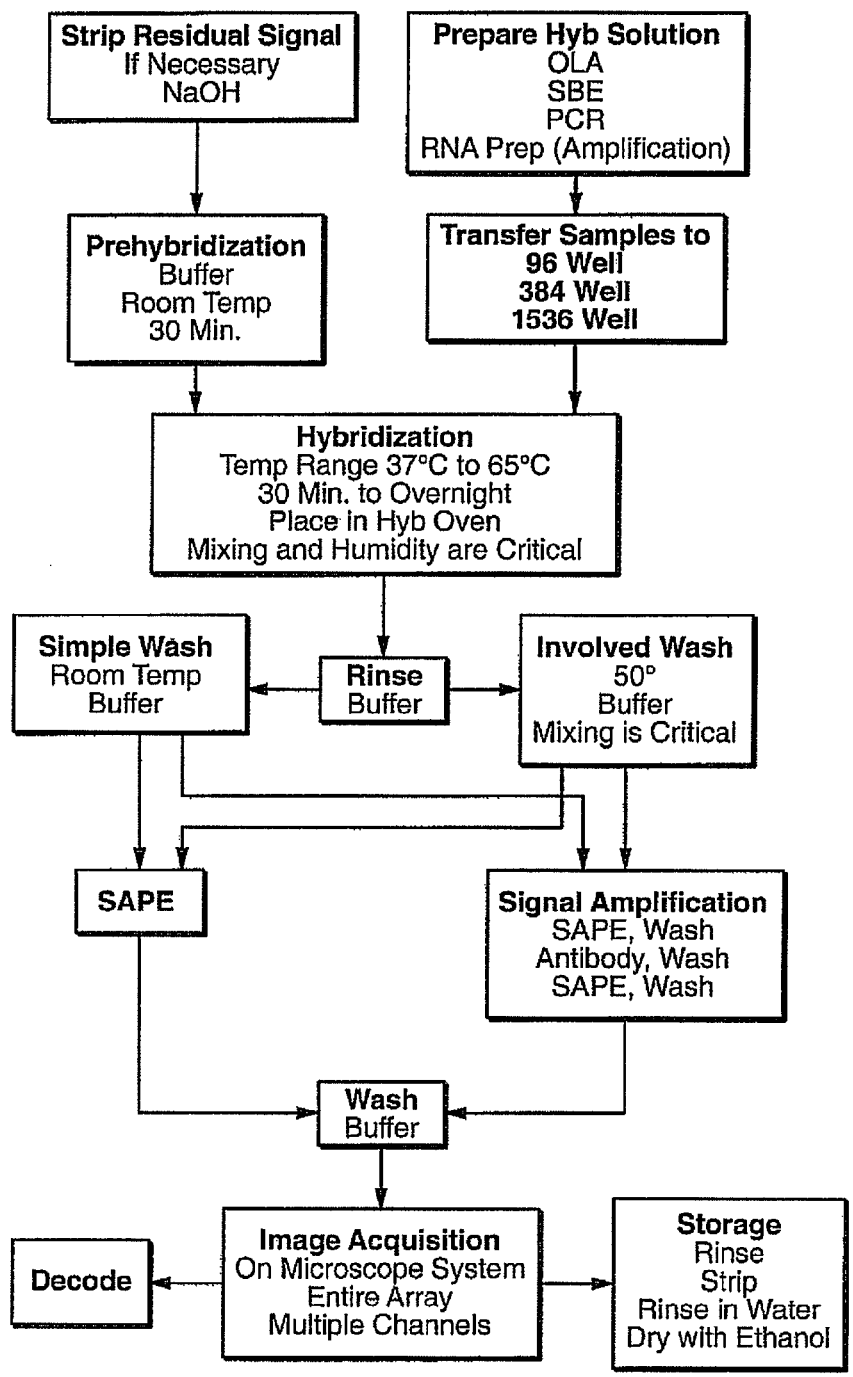
FIG._11

US 8,628,952 B2

ARRAY KITS AND PROCESSING SYSTEMS

RELATED APPLICATIONS

This application is a continuation of U.S. patent application Ser. No. 10/767,249, entitled METHODS OF MAKING AND USING COMPOSITE ARRAYS FOR THE DETECTION OF A PLURALITY OF TARGET ANALYTES, filed Jan. 28, 2004, now U.S. Pat. No. 7,510,841, issued Mar. 31, 2009, which is a continuation of U.S. patent application Ser. No. 09/606,369, entitled COMPOSITE ARRAYS UTILIZING MICROSPHERES WITH A HYBRIDIZATION CHAMBER, filed Jun. 28, 2000, now abandoned. The disclosures of each of the above patents and patent applications are incorporated herein by reference in their entireties.

FIELD OF THE INVENTION

The invention relates to sensor compositions comprising a composite array of individual arrays, to allow for simultaneous processing of a number of samples. The invention further provides methods of making and using the composite arrays. The invention further relates to an apparatus comprising a hybridization chamber for holding composite arrays.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads go down randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

In addition, compositions comprising silicon wafers comprising a plurality of probe arrays in microtiter plates have been described in U.S. Pat. No. 5,545,531.

SUMMARY OF THE INVENTION

In accordance with the above objects, the present invention provides composite array compositions comprising a first substrate with a surface comprising a plurality of assay locations, each assay location comprising a plurality of discrete sites. The substrate further comprises a population of microspheres comprising at least a first and a second subpopulation, wherein each subpopulation comprises a bioactive agent. The microspheres are distributed on each of the assay locations.

In a further aspect, the invention provides composite array compositions comprising a first substrate with a surface comprising a plurality of assay locations and a second substrate comprising a plurality of array locations, each array location comprising discrete sites. The compositions further comprise a population of microspheres comprising at least a first and a second subpopulanon, wherein each subpopulation comprises a bioactive agent. The microspheres are distributed on each of the array locations.

In an additional aspect, the present invention provides methods of decoding an array composition comprising providing an array composition as outlined above, and adding a plurality of decoding binding ligands to the composite array composition to identify the location of at least a plurality of the bioactive agents.

In a further aspect, the present invention provides methods of determining the presence of one or more target analytes in one or more samples comprising contacting the sample with a composition as outlined herein, and determining the presence or absence of said target analyte.

In a further aspect the invention provides a hybridization chamber. The hybridization chamber includes a base plate and a lid. A sealant is localized between the lid and base plate to provide for an airtight seal. When a two-component array system is used, the chamber also includes component ports in the lid to immobilize the array components. That is, array components are inserted through the port in the lid. The ports may include seals so that an airtight seal is maintained. The chamber also may include clamps and alignment pins.

In a further aspect the invention provides a hybridization chamber wherein the base plate contains holes. The holes may be in a microplate array format. In one embodiment at least two holes are joined by a channel. In one embodiment a flexible membrane is placed on the base plate. When pressure i.e. a vacuum, is applied to the membrane, wells form in the membrane at the location of the holes in the base plate. The apparatus also includes a pneumatic device for the delivery of a vacuum or positive pressure to the membrane.

In a further aspect the invention provides a method of mixing samples in an array formal. The method includes providing a vacuum to the membrane such that wells are formed. A solution is then applied to the membrane such that at least one of the wells is filled with liquid. Subsequently, the vacuum is applied intermittently to the membrane, which results in mixing of the liquid.

In a further aspect the invention provides an apparatus comprising a hybridization chamber as described herein and any of the composite array compositions described herein.

In a further aspect the invention provides performing methods of decoding an array composition as described herein in a hybridization chamber as described herein.

In a further aspect the invention provides performing methods of determining the presence of one or more target analytes in one or more samples as described herein in a hybridization chamber as described herein.

BRIEF DESCRIPTION OF THE FIGURES

FIGS. 1A, 1B, 1C, 1D and 1E depict several different "two component" system embodiments of the invention. In FIG. 1A, a bead array is depicted. The first substrate 10 has array locations 20 with wells 25 and beads 30. The second substrate 40 has assay locations 45. An optional lens or filter 60 is also shown; as will be appreciated by those in the art, this may be internal to the substrate as well. FIG. 1B is similar except that beads are not used; rather, array locations 20 have discrete sites 21, 22, 23, etc. that may be formed using spotting, printing, photolithographic techniques, etc. FIGS. 1C-F depict the use of a plurality of first substrates. FIG. 1C depicts a "bead of beads" that may have additional use for mixing functions. FIG. 1D depicts a plurality of bead arrays and FIG. 1E depicts a plurality of non-bead arrays. FIG. 1F depicts the use of binding functionalities to "target" first substrates 10 to locations on the second substrate 40; as will be appreciated by those in the art, this may be done on flat second substrates or on compartmentalized second substrates. FIG. 1F utilizes binding ligand pairs 70/70', 71/71', 72/72', etc. These may be either chemical functionalities or biological ones, such as are described for IBL/DBL pairs, such as oligonucleotides, etc.

FIGS. 2A and 2B depict two different "one component" systems. FIG. 2A depicts a bead array, with the substrate 50 having assay locations 45 with wells 25 comprising beads 30. FIG. 2B depicts a non-bead array; each assay location 45 has discrete sites 21, 22, 23, etc.

FIG. 3 depicts clustering in hyperspectral alpha space ($\alpha_1=I_1/\Sigma I_i$, $\alpha_2=I_2/\Sigma I_i$, $\alpha_3=I_3/\Sigma I_i$, etc.). A set of 128 different bead types present on a fiber bundle were decoded with by hybridizing set of complementary oligonucleotides labeled with four dyes: Bodipy-493, Bodipy-R6G, Bodipy-TXR, and Bod-564 (only one dye per oligonucleotide). Shown is the second stage of a four stage decode in which 4013 beads were decoded. Ovals are drawn around zones of hue clusters.

FIG. 5 depicts the decoding 128 different bead types with four colors and four decode stages. (inset shows a single decode stage using four different dyes to decode 16 bead types.)

FIG. 6 depicts grey scale decoding of 16 different bead types. (A) Combinatorial pooling scheme for complementary decoding oligos. A (B) Two independent normalizing images were acquired, and the resulting bead intensities compared. (C) The alpha values (ratio of bead intensity in indicated decode stage to intensity in normalization image) are plotted for three decodes stage described in (A).

FIG. 7 schematically depicts the lid and base plate. A. Depicts the lid 10 and base plate 60 of the hybridization chamber. Ports 20 in the lid allow for fiber optic bundles 30 to be inserted through the lid and contact the sample in the wells of the microtiter plate 40 in the base cavity 50 of the base plate 60. B. Depicts the base cavity 50 of the base plate 60.

FIG. 8 schematically depicts the hybridization chamber including the lid 10 and base plate 60. Also shown are the peripheral seal 80, the clamp 90 and clamp receptacle 95, fiber optic bundles 30 inserted through the lid and into the well of the microtiter plate 40.

FIG. 9 depicts a base plate with holes 105. A Depicts the holes 105 in the base plate. B Depicts channels 100 connecting the holes 105.

FIG. 10 depicts variable solution volume and localization on the membrane caused by pressure and/or vacuum. A. +P indicates pressure; −P indicates vacuum. Upward bending of the membrane in response to pressure in all chambers and holes. B. Fluid is moved to the left side of the membrane when vacuum is applied to the left chambers and pressure is applied to the middle and right chambers. C. When vacuum is first applied to the left section, fluid fills the wells. When vacuum is subsequently applied to the middle and right chambers, empty wells are formed. D. Fluid moves to the center of the membrane when vacuum is applied to the center and pressure is applied to left and right chambers. E. Fluid fills in wells formed by high vacuum in the center. Empty wells form on the left and right when low vacuum is applied. F. Fluid moves to the right when vacuum is applied to the right chamber and pressure is applied to the left and middle chambers.

FIG. 11 depicts a flow chart of a representative assay scheme that finds use with the hybridization chamber.

DETAILED DESCRIPTION OF THE INVENTION

Figure 4:
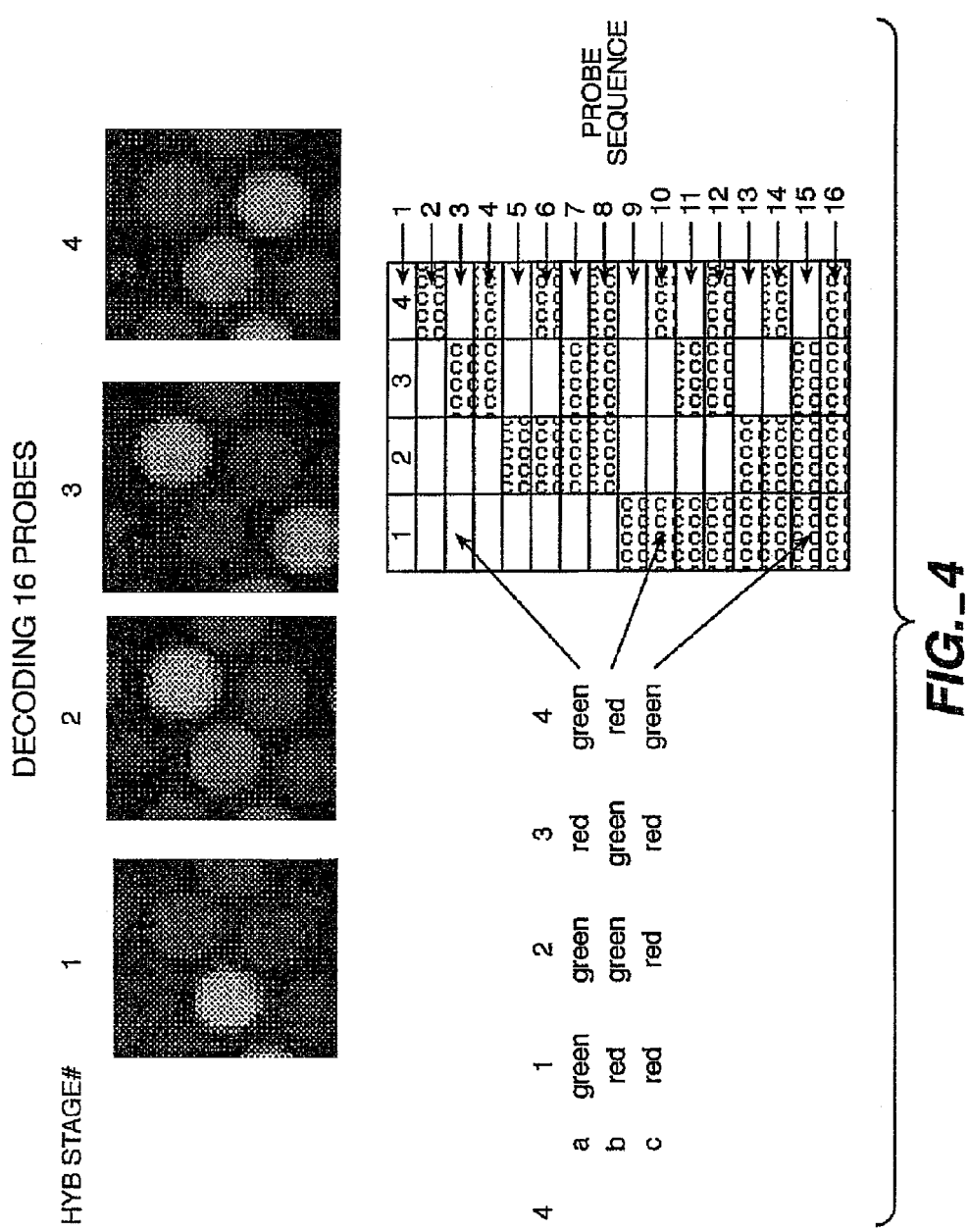
FIG. 4 Illustrates a two color decoding process wherein either FAM-labeled or Cy3-labeled oligo complements are use to "paint" (label) the different bead types on the array.

The present invention is directed to the formation of very high density arrays that can allow simultaneous analysis, i.e. parallel rather than serial processing, on a number of samples. This is done by forming an "array of arrays", i.e. a composite array comprising a plurality of individual arrays, that is configured to allow processing of multiple samples. For example, each individual array is present within each well of a microtiter plate. Thus, depending on the size of the microtiter plate and the size of the individual array, very high numbers of assays can be run simultaneously; for example, using individual arrays of 2,000 distinct species (with high levels of redundancy built in) and a 96 well microtiter plate, 192,000 experiments can be done at once; the same arrays in a 384 microtiter plate yields 768,000 simultaneous experiments, and a 1536 microtiter plate gives 3,072,000 experiments.

Generally, the array compositions of the invention can be configured in several ways. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing bioactive agents can then be loaded into the bead wells in each assay location as is more fully described below. It should be noted that while the disclosure herein emphasizes the use of beads, beads need not be used in any of the embodiments of the invention; the bioactive agents can be directly coupled to the array locations. For example, other types of arrays are well known and can be used in this format; spotted, printed or photolithographic arrays are well known; see for example WO 95/25116; WO 95/35505; PCT US98/09163; U.S. Pat. Nos. 5,700,637; 5,807,522 and 5,445,934; and U.S. Ser. Nos. 08/851,203, 09/187,289; and references cited within, all of which are expressly incorporated by reference. In one component systems, if beads are not used, preferred embodiments utilize non-silicon wafer substrates.

Alternatively, a "two component" system can be used. In this embodiment, the individual arrays are formed on a second substrate, which then can be fitted or "dipped" into the first microtiter plate substrate. As will be appreciated by those in the art, a variety of array formats and configurations may be utilized. A preferred embodiment utilizes fiber optic bundles as the individual arrays, generally with a "bead well" etched into one surface of each individual fiber, such that the beads containing the bioactive agent are loaded onto the end of the fiber optic bundle. The composite array thus comprises a number of individual arrays that are configured to fit within the wells of a microtiter plate. Alternatively, other types of array formats may be used in a two component system. For example, ordered arrays such as those made by spotting, printing or photolithographic techniques can be placed on the second substrate as outlined above. Furthermore, as shown in FIGS. 1C-F, "pieces" of arrays, either random or ordered, can be utilized as the first substrate.

The present invention is generally based on previous work comprising a bead-based analytic chemistry system in which beads, also termed microspheres, carrying different chemical functionalities are distributed on a substrate comprising a patterned surface of discrete sites that can bind the individual microspheres. The beads are generally put onto the substrate randomly, and thus several different methodologies can be used to "decode" the arrays. In one embodiment, unique optical signatures are incorporated into the beads, generally fluorescent dyes, that could be used to identify the chemical functionality on any particular bead. This allows the synthesis of the candidate agents (i.e, compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art. These methods are generally outlined. in PCT US98/05025; PCT US98/21193; PCT US99/20914; PCT US99/14387; and U.S. Ser. Nos. 08/818, 199; 09/315,584; and 09/151,877, all of which are expressly incorporated herein by reference. In addition, while the discussion herein is generally directed to the use of beads, the same configurations can be applied to cells and other particles; see for example PCT US99/04473.

In these systems, the placement of the bioactive agents is generally random, and thus a coding/decoding system is required to identify the bioactive agent at each location in the array. This may be done in a variety of ways, as is more fully outlined below, and generally includes: a) the use a decoding binding ligand (DBL), generally directly labeled, that binds to either the bioactive agent or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target analyte. Similarly, this may occur either prior to or after addition of a target analyte.

Once the identity (i.e. the actual agent) and location of each microsphere in the array has been fixed, the array is exposed to samples containing the target analytes, although as outlined below, this can be done prior to or during the analysis as well. The target analytes will bind to the bioactive agents as is more fully outlined below, and results in a change in the optical signal of a particular bead.

In the present invention, "decoding" can use optical signatures, decoding binding ligands that are added during a decoding step, or a combination of these methods. The decoding binding ligands will bind either to a distinct identifier binding ligand partner that is placed on the beads, or to the bioactive agent itself, for example when the beads comprise single-stranded nucleic acids as the bioactive agents. The decoding binding ligands are either directly or indirectly labeled, and thus decoding occurs by detecting the presence of the label. By using pools of decoding binding ligands in a sequential fashion, it is possible to greatly minimize the number of required decoding steps.

Accordingly, the present invention provides composite array compositions comprising at least a first substrate with a surface comprising a plurality of assay locations. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, (with all numbers being per square centimeter) with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 μm or less (with beads of 200 nm possible) can be used, and very small fibers are known, it is possible to have as many as 40,000-50,000 or more (in some instances, 1 million) different fibers and beads in a 1 mm$^2$ fiber optic bundle, with densities of greater than 15,000,000 individual beads and fibers (again, in some instances as many as 25-50 million) per 0.5 cm$^2$ obtainable.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics. In some embodiments, silicon wafer substrates are not preferred. In one embodiment the substrate is in the shape of or is a microscope slide.

The first substrate comprises a surface comprising a plurality of assay locations, i.e. the location where the assay for the detection of a target analyte will occur. The assay locations are generally physically separated from each other, for example as assay wells in a microtiter plate, although other configurations (hydrophobicity/hydrophilicity, etc.) can be used to separate the assay locations.

In a preferred embodiment, the second substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

However, in some "two component" embodiments, the second substrate is not a fiber optic array.

In a preferred embodiment, the assay locations (of the "one component system") or the array locations (of the "two component system") comprise a plurality of discrete sites. Thus, in the former case, the assay location is the same as the array location, as described herein. In the latter case, the array location is fitted into the assay location separately. In these embodiments, at least one surface of the substrate is modified to contain discrete, individual sites for later association of microspheres (or, when microspheres are not used, for the attachment of the bioactive agents). These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate. When the first substrate comprises both the assay locations and the individual arrays, a preferred method utilizes molding techniques that form the bead wells in the bottom of the assay wells in a microtiter plate. Similarly, a preferred embodiment utilizes a molded second substrate, comprising "fingers" or projections in an array format, and each finger comprises bead wells.

In a preferred embodiment, physical alterations are made in a surface of the substrate to produce the sites. In a preferred embodiment, for example when the second substrate is a fiber optic bundle, the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain modified sites, particularly chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites.

In addition, biologically modified sites may be used to attach beads to the substrate. For example, binding ligand pairs as are generally described herein may be used; one partner is on the bead and the other is on the substrate. Particularly preferred in this embodiment are complementary nucleic acid strands and antigen/antibody pairs.

Furthermore, the use of biological moieties in this manner allows the creation of composite arrays as well. This is analogous to the system depicted in FIG. 1F, except that the substrate 10 is missing. In this embodiment, populations of beads comprise a single binding partner, and subpopulations of this population have different bioactive agents. By using different populations with different binding partners, and a substrate comprising different assay or array locations with spatially separated binding partners, a composite array can be generated. This embodiment also a reuse of codes, as generally described below, as each separate array of the composite array may use the same codes.

As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

As will be appreciated by those in the art, there are a number of possible configurations of the system, as generally depicted in the Figures. In addition to the standard formats described herein, a variety of other formats may be used. For example, as shown in FIGS. 1C-1F, "pieces" of substrates may be used, that are not connected to one another. Again, these may be the same arrays or different arrays. These pieces may be made individually, or they may be made as a large unit on a single substrate and then the substrate is cut or separated into different individual substrates. Thus, for example, FIGS. 1C and 1D depict a plurality of bead arrays that are added to the wells of the second substrate; FIG. 1C is a "bead of beads" that is configured to maximize mixing. FIG. 1D utilizes a plurality of planar first substrates; as will be appreciated by those in the art, these may or may not be attached to the second substrate. In one embodiment, no particular attachment means are used; alternatively, a variety of attachment techniques are used. For example, as outlined for attachment of beads to substrates, covalent or non-covalent forces may be used, including the use of adhesives, chemistry, hydrophobic/hydrophilic interactions, etc. In addition, the substrate may be magnetic and held in place (and optionally mixed) magnetically as well. Thus, for example, as depicted in FIG. 1F, binding moieties can be used; these can be covalent linkages or non-covalent linkages. They may be used simply for attachment, or for targeting the first substrate arrays to particular locations in or on the second substrate. Thus, for example, different oligonucleotides may be used to target and attach the first substrate to the second.

In a preferred embodiment, there are optical properties built into the substrate used for imaging. Thus, for example, "lensing" capabilities may be built into the substrate, either in a one component or two component system. For example, in a one component system, the bottom of one or more of the assay locations may have unique or special optical components, such as lenses, filters, etc.

In addition, preferred embodiments utilize configurations that facilitate mixing of the assay reaction. For example, preferred embodiments utilize two component systems that allow mixing. That is, in some embodiments, the arrays project from the block and can be used as a "stick" that stirs the reaction to facilitate good mixing of the assay components, increase the kinetics of the reaction, etc. As will be appreciated by those in the art, this may be accomplished in a variety of ways. In a preferred embodiment, the first and second substrates are configured such that they can be moved relative to one another, either in the X-Y coordinate plane, the X-Z coordinate plane, the Y-Z coordinate plane, or in three dimensions (X-Y-Z). Preferred embodiments utilize a block jig that allows the block to move freely in either the plane of the plate or orthogonal to it. This is particularly useful when the reaction volumes are small, since standard mixing conditions frequently do not work well in these situations.

In addition to this, or in place of it, there may be additional mixing components as part of the system. For example, there may be exogeneous mixing particles added; one embodiment for example utilizes magnetic particles, with a magnet that is moved to force mixing; for example small magnetic mixing bars and magnetic stir plates may be used.

Alternatively, mixing in either one or two component systems can be accomplished by sealing the system and shaking it using standard techniques, optionally using mixing particles.

In a preferred embodiment, the system is configured to reduce evaporation and facilitate small sample size and handling. That is, the system is closed or sealed by enclosing a defined space to maintain control over the small sample volumes. In this regard the invention provides a hybridization chamber that encompasses or encloses the array and/or sample. As is more fully outlined below, preferred embodiments utilize the hybridization chambers comprising a base plate and alignment moieties that find particular use in the two-component system, although they also find use in the one-component system.

One advantage of the enclosed system is that it reduces or dampens vibration. That is, because of the small sample volume, the arrays may be susceptible to disturbances caused by vibration, for example, by platform shaking, motor vibration, or air circulation. By enclosing the array, and placing the array on the base plate, the samples and arrays are less susceptible to disturbances caused by vibration as the base plate dampens the vibration.

An additional advantage of this aspect of the invention is that the enclosed array allows for the use of increasingly small volumes. In an open array format, small sample volumes may evaporate resulting in a variety of problems including sample variation, alteration and inconsistent concentration of solutes in the solution. For example, when small sample volumes are present in different assay locations, differential evaporation of the solution may result in dramatically altered solute concentration. Such differences may alter hybridization kinetics, for example, and make it difficult to interpret and compare results obtained from such open arrays. However, by enclosing the array, for example in the hybridization chamber outlined herein, such sample variance is minimized thereby rendering the data obtained from the enclosed array more reliable. Accordingly, any of the methods described herein, find use with the hybridization chamber.

Also, the enclosed array allows for prolonged assay/incubation times relative to incubation times in an open array. Again, the sealed or enclosed array prevents sample evaporation, allowing for prolonged incubation periods.

In addition, the enclosed array facilitates mixing of the sample, when necessary. In general, when using small sample volumes, adequate mixing of the sample may be difficult to achieve. However, as is more fully outlined below, in one embodiment the hybridization chamber facilitates mixing when flexible membranes are used with a pneumatic device that provides vacuum and/or pressure.

When a "two-component" system is used, a hybridization chamber may be used. That is, both of the components i.e. the substrate comprising a plurality of assay locations and the substrate comprising a plurality of array locations, are enclosed within the hybridization chamber. In a preferred embodiment, these components include but are not limited to a fiber optic array and a multi-well microtiter plate that are enclosed in the hybridization chamber.

In a preferred embodiment the hybridization chamber contains a base plate upon which or into which one of the components is placed. By base plate is meant any platform or holder onto which one of the array components is placed. The base plate may be made of any material including plastic, glass or metal or any materials outlined herein for substrates; when the base plate is metal, it is preferably made of aluminum. Aluminum provides for a light weight yet durable base plate. In addition, aluminum allows for efficient and/or rapid heat transfer to the chamber. However, when the base plate is made of plastic or glass, the component is directly contacted with the base plate. Alternatively, metal sheets or templates may be inserted into or placed on the base plate. The metal sheets or templates can be designed to hold any of a variety of shapes to accommodate a variety of component sizes and/or shapes. As previously described, metal offers the advantage of being a rapid and efficient heat conductor.

In one embodiment the base plate contains at least one depression or base cavity into which the array component is placed. That is, when a microtiter plate is the component, for example, the depression or base cavity is formed such that the microtiter plate is placed directly into it and preferably fits tightly to avoid extra vibration and allow efficient heat transfer. The depression may be molded into the base plate. In addition, the base plate may contain multiple depressions or cavities such that multiple separate array components are placed on a single base plate. Alternatively, the base plate may be flat, and preferably comprise hooks or other attachment moieties to keep the arrays in place.

In addition preferred embodiments utilize a lid with the hybridization chamber. The lid can be made of any material (again, as listed for substrates herein), but glass, plastics or metal is preferred. The lid is preferably matched to the base plate such that when the lid is placed on the base plate, a closed chamber is formed.

In another embodiment the lid comprises at least one component placement port. By component placement port is meant a site in the lid to which a component is immobilized. That is, the placement port allows for attachment of one of the components to the lid. In a preferred embodiment, the port is a hole in the lid through which the component is inserted. For example, when a fiber optic bundle is the component, the bundle is inserted through the port. In this embodiment, the port additionally comprises a sealant surrounding the attachment site, such that an airtight seal is formed between the component, i.e. the distal end of the fiber optic bundle, and the lid. This sealant may be any material including silicon, rubber, plastic, etc., as outlined below. Alternatively, the seal may be a gel-based substance such as petroleum jelly, or a film based substance such as PARAFILM.

In an additional embodiment, the lid comprises a plurality of ports in the lid. That is, when multiple components are to be used, it is necessary to have a separate port for each component. For example, when multiple fiber optic bundles are used, each fiberoptic bundle is placed in a separate port. However, although it is possible for each fiber optic bundle to be inserted into one port at a time, it is also possible for the same fiber optic bundle to be inserted into different ports successively. That is, there is nothing to limit the number of ports into which a component is inserted successively. For example, as shown in FIG. 7A the lid 10 contains multiple ports 20 into which fiber optic bundles 30 are placed. The lid is then placed onto a microtiter plate 40 in the base cavity 50 of the base plate 60. A base plate 60 is depicted in FIG. 7*b* and shows the base plate 60 and base cavity 50.

In a preferred embodiment, the port seal reduces or prevents solution cross contamination. That is, the seal surrounding the individual port/component forms a seal against the base plate or array component such that the solution from the sample corresponding to a particular port/component is separated or sealed from the other components.

In an alternative embodiment, not all ports are filled with components at all times. When it is appropriate or desired to have less than maximal filling of the ports, plugs can be inserted into the ports that do not contain components. In this manner, the lid still forms an airtight seal with the base plate, despite the presence of ports without components. The plugs can be in the form of a rubber stopper, a gasket, a film, a gel and the like.

In a preferred embodiment around the periphery of the chamber between the lid and base plate resides a sealant. The sealant may be of any material that results in an airtight seal being formed between the lid and base plate. In a preferred embodiment, the sealant is formed of rubber, such as a rubber or silicon gasket or O-ring 80 (see FIG. 8). The sealant may be fixed to either the lid or baseplate. To this end, the sealant may be permanently affixed to the lid or baseplate. Alternatively, the sealant may fit into a groove in either the lid or base plate. As such, the sealant is immobilized to the lid or base plate, but the immobilization is not necessarily permanent. Alternatively, the sealant may be formed from a liquid sealant such as petroleum jelly or from a pliable film material such as PARAFILM or other waxes.

In a preferred embodiment, when a two-component system is used, the hybridization chamber further comprises alignment moieties. By alignment moieties is meant a feature of the chamber that facilitates alignment of the lid with the base plate. The importance of the alignment moieties resides not only in the alignment of a single lid and base plate, but also reproducible alignment of multiple lids and base plates. That is, the alignment moieties facilitate the physical alignment between any array components and any multiple well microtiter plate configuration. When fiber optic bundles in the lid are to be aligned with a microtiter plate on the base plate, the alignment moieties allow for alignment of the vertical center axis of the fiber bundle with their corresponding well center axis. In a preferred embodiment, alignment is such that all fiber bundles clear, i.e. do not touch, the inner walls of the wells. This alignment may be important for sequential imaging.

In one embodiment the alignment moiety is a complementary male/female fitting. The male fitting may be affixed to the lid or base plate, although it need not be permanently affixed. When a male fitting is used as an alignment moiety in either the base plate or lid of the chamber, it is preferable that the opposite chamber piece contain a slot or hole (female fitting) into which the male fitting is inserted. One of ordinary skill in the art appreciates the variations of this male/female fitting that find use with the invention. In this regard, the features may be indexer pins or bumps on one chamber piece and holes or complementary grooves on the other piece.

In a preferred embodiment, fiducials are used; see U.S. Ser. Nos. 60/119,323, and 09/500,555 and PCT/US00/03375, hereby incorporated by reference in their entirety.

In an alternative embodiment, the chamber may also contain clamp features to maintain secure contact between the lid and base plate. The advantage of clamping is to distribute uniform loading throughout the chamber to accomplish uniform seal compression. By "clamp features" or "clamps" is meant any feature that allows for the application and maintenance of increased pressure or a seal between the lid and base plate. In one embodiment, the claim feature includes a rotating stud/receptacle mechanism. That is, a stud 90 is inserted into a receptacle 95 and rotated to depress the lid and base plate together (see FIG. 8). Alternatively, the mechanism may include a hook and latch mechanism. One of ordinary skill in the art appreciates the number of clamping mechanisms that find use with the invention. In addition, one of ordinary skill in the art appreciates that the method of clamping is not limited to manual clamping. As such, it may also be automated.

In an alternative embodiment, the chamber includes features around the periphery for handling the chamber. In a preferred embodiment the features are slots that are wide enough to permit a users fingers to manually handle the chamber/array. In an alternative embodiment, the features are slots, grooves, handles and the like and may find particular use in automatic or robotic movement of the chambers. These additional features may also be distributed asymmetrically to facilitate robotic handling.

As described above, an advantage of the hybridization chamber is that small sample volumes can be used without the loss of sample solution. In a further embodiment, the chamber may contain one or more reservoirs to hold additional solutions. As such, the hybridization chamber also functions as a humidity chamber. The inclusion of additional solution in the reservoir further prevents evaporation of sample.

In an alternative embodiment, for example when no microtiter plate is used, the sample may be applied to a membrane that is on the surface of a base plate. Advantages of using the membrane include ease of cleaning or even disposing of the membrane after each use and the flexible membrane will not damage pipette tips or fiber optic tips due to contacting the tips with the bottom of the sample well.

In this embodiment, the base plate contains a series of small openings 105, for example in microplate format (FIG. 9A). Thus, the membrane is depressed into the openings forming separate assay locations. A variety of membranes are useful with the invention. What is important is that the membrane is flexible. In some embodiments it may be desired to have a chemically inert membrane, while in some embodiments it may be desirable to have a membrane to which assay components will interact, for example nylon, nitrocellulose membranes and the like.

In a preferred embodiment, channels connect each of the openings (FIG. 9B). The channels 100 may connect to a pneumatic device that produces vacuum and/or pressure. Thus, when vacuum is applied, the membrane deforms into the openings 105 to form small pockets or wells. The sample can then be applied to the pockets. By applying different amounts of vacuum to the membrane through the openings, the volume of the well formed by the deformed membrane and fluid height can be changed. Furthermore, applying intermittent vacuum to the membrane through the channel can also agitate or mix the liquid in the wells. Such a mixing method is advantageous because the entire system does not have to be vibrated and stir bars or tumblers are not required. Furthermore, when subsets of openings are connected to different channels, different subsets can be mixed independently in the same base plate.

When positive pressure is applied, the membrane deforms up or stays flat depending on the magnitude of the pressure, whether there is a load on top of the membrane and the size and shape of the opening. This has significant advantages particularly in washing or cleaning of the chamber.

When pressure and vacuum are applied to different ports in certain sequences, small amounts of solutions can be made to migrate to different portions of the membrane. That is, as shown in FIG. 10A-F, differential application of pressure and vacuum results in a membrane that is elevated in some places and depressed in other places. Thus, a solution that is applied to the membrane will migrate to the lower sections of the membrane. This has the advantage of allowing incubations of a sample on the membrane to proceed for precise times. That is following the particular time, vacuum can be released and if necessary pressure applied to remove the solution. This will allow the incubation in small sections to achieve uniform incubation time between the first and last wells across an array.

Advantages of regulating sample volume through the application of vacuum or pressure, include reducing consumption volume of reagents, such as hybridization solutions; increasing the ease of mixing small sample volumes and increasing the ease of cleaning the membrane.

In a preferred embodiment the channels connect to common fluid handling devices to pump in or suck out sample solutions such as hybridization mixtures or wash fluids. Again, in one embodiment all openings are connected to a single channel. As such, all wells are treated with the same solution. Alternatively, subpopulations of openings are connected to different channels allowing for differential application of solutions to the subpopulations.

When the channels are connected to fluid handling devices, it will be necessary to include a feature for the application and removal of the liquid from the sample. That is, for liquid to be added and removed through the opening in the base plate, the membrane must be penetrated to allow the fluid to be moved. In this regard, a needle, for example, is useful for puncturing the membrane to apply and remove the fluid. When needles are used, it may be necessary to use a resealable membrane, or apply a sealant to the puncture location to prevent undesired leakage of the solution.

In some embodiments the chamber includes heat transfer features. That is, when elevated temperatures are required or desired, the chamber is designed to maintain elevated temperatures. In one embodiment, this includes the application of an insulating material to the chamber. Then, when pre-warmed solution is introduced into the chamber, the elevated temperature is maintained. That is, the solution can be easily heated outside of the chamber prior to being pumped into the chamber. The simple chamber geometry will facilitate the maintenance of equal temperatures between liquid in different wells.

In an alternative embodiment, the chamber includes a heating mechanism to maintain the elevated temperature in the chamber. In one embodiment, the chamber is heated uniformly by the heating apparatus. In an alternative embodiment, the heating apparatus heats different sections of the chamber independently.

As described above, the use of metal such as aluminum on the base plate facilitates heat transfer because the metal is a fast and efficient conductor of heat.

When a "one-component" system is used, a lid and a sealing mechanism can be used. That is, as described above, the lid forms an airtight seal with the base plate. Thus, like the lid above, the lid of the "one-component" system also includes a sealant between the lid and base plate. In one embodiment, the lid and base plate also include alignment moieties as described above for the "two-component" system. Alternatively, in one embodiment the chamber of the one-component system does not include alignment moieties. In this respect, the necessity for stringent alignment of the lid and base plate in the one-component system is lower than that for the two-component system. That is, because the one-component system does not have array components in the lid to be aligned with array locations on the base plate, alignment is not as stringent. However, alignment may still be important for imaging.

Furthermore, as described above, the lid of the chamber in the one-component system can be made of glass, plastic or metal. Again, the use of metal facilitates the maintenance of temperature as the metal is a fast and efficient heat conductor.

In addition, the system may comprise additional elements as well. These include a holder or holders for the probes or fiber optic bundles. Such holders are more fully described in U.S. Ser. No. 60/135,089, filed May 20, 1999, and Ser. No. 09/574,962 filed May 19, 2000, and PCT US00/13772 filed May 19, 2000. In addition, the system may include cells as described in U.S. Ser. Nos. 09/033,462 and 09/260,963 and PCT/US99/04473. In addition, the system may include fiducials as described in U.S. Ser. Nos. 60/119,323, and 09/500,555 and PCT/US00/03375, all of which are expressly incorporated herein by reference.

In a preferred embodiment, the methods and compositions of the invention comprise a robotic system. Many systems are generally directed to the use of 96 (or more) well microtiter plates, but as will be appreciated by those in the art, any number of different plates or configurations may be used. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic systems include automated liquid- and particle-handing, including high throughput pipetting to perform all steps of screening applications. This includes liquid, and particle manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid and particle transfers.

In a preferred embodiment, chemically derivatized particles, plates, tubes, magnetic particle, or other solid phase matrix with specificity to the ligand or variant proteins are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.

In a preferred embodiment, Interchangeable pipet heads (single or multi-channel) with single or multiple magnetic probes, affinity probes, or pipetters robotically manipulate the liquid and particles. Multi-well or multi-tube magnetic separators or platforms manipulate liquid and particles in single or multiple sample formats.

In some preferred embodiments, the instrumentation will include CCD cameras to capture and transform data and images into quantifiable formats; and a computer workstation. These will enable data analysis.

The flexible hardware and software allow instrument adaptability for multiple applications. The software program modules allow creation, modification, and running of methods. The system diagnostic modules allow instrument alignment, correct connections, and motor operations. The customized tools, labware, and liquid and particle transfer patterns allow different applications to be performed. The database allows method and parameter storage. Robotic and computer interfaces allow communication between instruments.

In a preferred embodiment, the robotic workstation includes one or more heating or cooling components. Depending on the reactions and reagents, either cooling or heating may be required, which can be done using any number of known heating and cooling systems, including Peltier systems.

In a preferred embodiment, the robotic apparatus includes a central processing unit which communicates with a memory and a set of input/output devices (e.g., keyboard, mouse, monitor, printer, etc.) through a bus. The general interaction between a central processing unit, a memory, input/output devices, and a bus is known in the art. Thus, a variety of different procedures, depending on the experiments to be run, are stored in the CPU memory.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers Ind. is a helpful guide.

The beads need not be spherical; irregular particles may be used. In addition, the beads may be porous, thus increasing the surface area of the bead available for either bioactive agent attachment or IBL attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et. al., *J. Am. Chem. Soc.*, 111:2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et. al., *Nature*, 380:207 (1996), all of which are incorporated by reference)). Other analog nucleic acids include those with positive backbones (Denpcy, et. al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Int. Ed. English*, 30:423 (1991); Letsinger, et al., *J. Am. Chem. Soc.*, 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

In a preferred embodiment, the bioactive agents are libraries of clonal nucleic acids, including DNA and RNA.

In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiterplate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the beads. For example, cloned nucleic acids can be derivatized, for example with one member of a binding pair, and the beads derivatized with the other member of a binding pair. Suitable binding pairs are as described herein for IBL/DBL pairs. For example, the cloned nucleic acids may be biotinylated (for example using enzymatic incorporate of biotinylated nucleotides, for by photo-activated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can then be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, special methods are required to decode clonal arrays, as is more fully outlined below.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarily need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., *Molecular Cloning: A Laboratory Manual*, 2d Edition, 1989, and *Short Protocols in Molecular Biology*, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$ 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art, In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems*, 7(4):275-308 (1991), expressly incorporated herein). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target. In addition, these types of chemical or biological functionalities may be used to attach arrays to assay locations, as is depicted in FIG. 1F, or individual sets of beads.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant)-0.02%, and rinsed again with a pH 7.7 PBS plus 0.01% tween 20. Finally, the enzyme is added to the solution, preferably after being prefiltered using a 0.45 µm amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids (including nucleic acid molecules that form triple helices), and carbohydrates and their binding partners are also suitable binding pairs. Nucleic acid—nucleic acid binding proteins pairs are also useful, including single-stranded or double-stranded nucleic acid binding proteins, and small molecule nucleic acid binding agents. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the bioactive agent are the same moiety; thus, for example, as outlined herein, particularly when no optical signatures are used, the bioactive agent can serve as both the identifier and the agent. For example, in the case of nucleic acids, the beadbound probe (which serves as the bioactive agent) can also bind decoder probes, to identify the sequence of the probe on the bead. Thus, in this embodiment, the DBLs bind to the bioactive agents.

This is particularly useful as this embodiment can give information about the array or the assay in addition to decoding. For example, as is more fully described below, the use of the DBLs allows array calibration and assay development. This may be done even if the DBLs are not used as such; for example in non-random arrays, the use of these probe sets can allow array calibration and assay development even if decoding is not required.

In a preferred embodiment, the microspheres do not contain an optical signature. That is, as outlined in U.S. Ser. Nos. 08/818,199 and 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Thus, the present invention need not rely solely on the use of optical properties to decode the arrays, although in some instances it may. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use in combination with optical signatures one beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further increased if another parameter is included such as concentration or intensity; thus for example, if two different concentrations of the IBL are used, then the array size increases as $3^n$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

Once the microspheres comprising the candidate agents and the unique IBLs are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target analytes, prior to the addition of the beads to the substrate; after addition and assay, the array may be decoded. This is particularly preferred when the sample comprising the beads is agitated or mixed; this can increase the amount of target analyte bound to the beads per unit time, and thus (in the case of nucleic acid assays) increase the hybridization kinetics. This may find particular use in cases where the concentration of target analyte in the sample is low; generally, for low concentrations, long binding times must be used.

In addition, adding the beads to the assay mixture can allow sorting or selection. For example, a large library of beads may be added to a sample, and only those beads that bind the sample may be added to the substrate. For example, if the target analyte is fluorescently labeled (either directly (for example by the incorporation of labels into nucleic acid amplification reactions) or indirectly (for example via the use of sandwich assays)), beads that exhibit fluorescence as a result of target analyte binding can be sorted via Fluorescence Activated Cell Sorting (FACS) and only these beads added to an array and subsequently decoded. Similarly, the sorting may be accomplished through affinity techniques; affinity columns comprising the target analytes can be made, and only those beads which bind are used on the array. Similarly, two bead systems can be used; for example, magnetic beads comprising the target analytes can be used to "pull out" those beads that will bind to the targets, followed by subsequent release of the magnetic beads (for example via temperature elevation) and addition to an array.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for association of the beads. This may be done in a variety of buffers, including aqueous and organic solvents, and mixtures. The solvent can evaporate, and excess beads removed.

In a preferred embodiment, when non-covalent methods are used to associate the beads to the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differential affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to associate the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface. FIG. 11 depicts a flow chart exemplifying, but not limiting, the assays that can be performed with the arrays and hybridization chamber of the invention.

In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags, or mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a nonfluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of association of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include luminescent labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference.

In one embodiment, the label is a molecule whose color or luminescence properties change in the presence of the IBL, due to a change in the local environment. For example, the label may be: (1) a fluorescent pH indicator whose emission intensity changes with pH; (2) a fluorescent ion indicator, whose emission properties change with ion concentration; or (3) a fluorescent molecule such as an ethidium salt whose fluorescence intensity increases in hydrophobic environments.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used in an assay, during the assay, or after the assay.

In one embodiment, a single decoding step is done. In this embodiment, each DBL is labeled with a unique label, such that the number of unique labels is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique label, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. Each pool of decoders contains only one of the n tag versions of each decoder, and no two decoder probes have the same sequence of tags across all the pools. The number of pools required for this to be true is determined by the number of decoder probes and the n. Hybridization of each pool to the array generates a signal at every address comprising an IBL. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

As will be appreciated by one of ordinary skill in the art, hybridization or incubation times vary. Generally, hybridization or incubation times last from seconds to minutes or up to hours or days or more. When the hybridization chamber as described herein is utilized, hybridization or incubation times can be increased relative to incubation times without the hybridization chamber.

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. As will be appreciated by those in the art, the decoder probes can be made in any order and added in any order.

In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include those listed for labeling DBLs, above.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same labels (i.e. telephone numbers) of other subarrays, that are separated by virtue of the location of the subarray. Thus, for example, the same unique labels can be reused from bundle to bundle. Thus, the use of 50 unique labels in combination with 100 different subarrays can form an array of 5000 different bioactive agents. In this embodiment, it becomes important to be able to identify one bundle from another; in general, this is done either manually or through the use of marker beads; these can be beads containing unique tags for each subarray, or the use of the same marker bead in differing amounts, or the use of two or more marker beads in different ratios.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the sub populations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency. Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes or "families" of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In a preferred embodiment, decoding of self-assembled random arrays is done on the bases of pH titration. In this embodiment, in addition to bioactive agents, the beads comprise optical signatures, wherein the optical signatures are generated by the use of pH-responsive dyes (sometimes referred to herein as "pH dyes") such as fluorophores. This embodiment is similar to that outlined in PCT US98/05025 and U.S. Ser. No. 09/15,877 both of which are expressly incorporated by reference except that the dyes used in the present invention exhibits changes in fluorescence intensity (or other properties) when the solution pH is adjusted from below the pKa to above the pKa (or vice versa). In a preferred embodiment a set of pH dyes is used, each with a different pKa, preferably separated by at least 0.5 pH units. Preferred embodiments utilize a pH dye set of pKa's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the bioactive agent is generated. Thus, the decoding of an array is achieved by titrating the array from pH 1 to pH 13, and measuring the fluorescence signal from each bead as a function of solution pH.

In a preferred embodiment, there are additional ways to increase the number of unique or distinct tags. That is, the use of distinct attributes on each bead can be used to increase the number of codes. In addition, sequential decoding allows a reuse of codes in new ways. These attributes are independent of each other, thus allowing the number of codes to grow exponentially as a function of the number of decoding steps and the number of attributes (e.g. distinct codes). However, by increasing the amount of decoding information obtained in a single decoding step, the number of decoding steps is markedly reduced. Alternatively, the number of distinct codes is markedly increased. By increasing the number of attributes per decoding step, fewer decoding steps are required for a given number of codes. Thus, in a preferred embodiment, a variety of methods are used to generate a number of codes for use in the process of decoding the arrays, while minimizing the necessary decoding steps. For example, a variety of different coding strategies can be combined: thus, different "colors", combinations of colors ("hues"), different intensities of colors or hues or both, etc. can all be combined.

In a preferred embodiment DBLs rely on attaching or embedding a quantitative or discrete set of physical attributes to the bead, i.e. labeling the bead. Preferred physical attributes of a bead include but are not limited to: surface "smoothness" or "roughness", color (Fluorescent and otherwise), color intensity, size, detectable chemical moieties, chemical reactivity, magnetization, pH sensitivity, energy transfer efficiency between dyes present, hydrophobicity, hydrophilicity, absorptivity, charge, pH sensitivity, etc.

A bead decoding scheme includes assigning/imbuing a single quantifiable attribute to each bead type wherein each bead type differs in the quantifiable value of that attribute. For instance, one can attach a given number of fluorophores to a bead and quantitate the number of attached fluorophores in the decoding process; however, in practice, attaching a "given amount" of an attribute to a bead and accurately measuring the attribute may be problematic. In general, the goal is to reduce the coefficient of variation (CV). By coefficient of variation is meant the variability in labeling a bead in successive labelings. This CV can be determined by labeling beads with a defined given number of label (fluorophore, for example) in multiple tests and measuring the resulting signal emitted by the bead. A large CV limits the number of useable and resolvable "levels" for any given attribute.

A more robust decoding scheme employs ratiometric rather than absolute measurements for segmenting a quantitative attribute into codes. By ratiometric decoding is meant labeling a bead with a ratio of labels (i.e. 1:10, 1:1, and 10:1). In theory any number of ratios can be used so long as the difference in signals between the ratios is detectable. This process produced smaller CVs and allowing more attribute segmentation within a given dynamic range. Thus, in a preferred embodiment, the use of ratiometric decoding reduces the coefficient of variability.

In addition, as will be appreciated by those in the art, ratiometric decoding can be accomplished in a different way. In this embodiment, rather than add a given number of DBLs with a first dye (or dye combination) intensity in the first decoding reaction and a second number with a second dye intensity in the sequential second decoding reaction, this ratiometric analysis may be done by using a ratio of labelled: unlabelled DBLs. That is, given a set saturating concentration of decoding beads, for example 100,000 DBLs/reaction, the first intensity decoding step may be done by adding 100,000 labelled DBLs and the second step can be done by adding 10,000 labelled DBLs and 90,000 unlabeled DBLs. Equilibrium dictates that the second step will give one tenth the signal intensity.

Because of the spread in values of a quantitatively measured attribute value, the number of distinct codes is practically limited to less than a dozen or so codes. However, by serially "painting" (i.e. temporarily attaching an attribute level to a bead) and "stripping" (removing the attribute level) a bead with different attribute values, the number of possible codes grows exponentially with the number of serial stages in the decoding process.

An example is illustrative. For instance, 9 different bead types and three distinguishable attribute distributions (Table 1). "Painting" (labeling) the beads with different attribute values in a combinatorially distinct pattern in the two different stages, generates a unique code for each bead type, i.e, nine distinct codes are generated. Thus, in a preferred embodiment beads are labeled with different attributes in a combinatorially distinct pattern in a plurality of stages. This generates unique codes for each bead type. Examples of different attributes are described above. Labeling of beads with different attributes is performed by methods known in the art.

TABLE 1

Serial decode generates unique codes using a small number of attribute levels.

| Bead Type | stage 1 attribute value | stage 2 attribute value | Code |
| --- | --- | --- | --- |
| 1 | L | L | (L, L) |
| 2 | L | M | (L, M) |
| 3 | L | H | (L, H) |
| 4 | M | L | (M, L) |
| 5 | M | M | (M, M) |
| 6 | M | H | (M, H) |
| 7 | H | L | (H, L) |
| 8 | H | M | (H, M) |
| 9 | H | H | (H, H) |

Number of unique codes = Number of attributes^Number of stages

Fluorescent colors are a particularly convenient attribute to use in a decoding scheme. Fluorescent colors can be attached to any agent that recognizes an IBL to form a labeled DBL. The discussion is directed to oligonucleotides (including nucleic acid analogs) as the DBLs. A fluorescently labeled oligonucleotide is a particularly useful DBL since it can specifically and reversibly "paint" (label) any desired subset of beads with a particular color simply by the process of hybridization and dehybridization (i.e. to the DBL with a complementary sequence). Moreover, fluorescence is easily imaged and quantitated using standard optical hardware and software. In order to "paint" a given bead type with a particular color, the bead type must be labeled with a unique hybridizable DNA sequence (IBL) and the decoding solution must contain the color-labeled complement of that sequence.

One consideration in implementing a decoding scheme is to minimize the number of images collected. In a color-based scheme, the number of images collected is the product of the number of colors and the number of stages. The number of images can be reduced by "painting" a bead with multiple colors for each given stage. By assigning multiple colors to a bead, the number of effective codes is increased. As an example, in a 24-bit three color scheme (e.g. red, green, blue) coloring process used by computers, a total of 256*256*256=16.7 million different "hues" can be generated from just three colors (red, green, blue).

Thus, in a preferred embodiment DBLs are labeled with a combination of colored fluorophores. As such, this method finds use in increasing the number of available codes for labeling DBLs using only a handful of different dyes (colors). Increasing the number of codes available at each decoding step will greatly decrease the number of decoding steps required in a given decoding process.

In one embodiment a population of oligonucleotides encoding a single DBL is labeled with a defined ratio of colors such that each bead to which the DBL binds is identified based on a characteristic "hue" formulated from the combination of the colored fluorophores. In a preferred embodiment two distinct colors are used. In a preferred embodiment, three or more distinct dyes (colors) are available for use. In this instance the number of differentiable codes generated by labeling a population of oligonucleotides encoding a single DBL with any given color is three. However by allowing combinations of colors and color levels in the labeling, many more codes are generated.

For decoding by hybridization, a preferred number of distinguishable color shades is from 2 to 2000; a more preferred number of distinguishable color shades is from 2 to 200 and a most preferred number of distinguishable color shades is from 2 to 20. Utilizing three different color shades (intensities) and three colors, the number of different hues will be $3^4=81$. Combining a hue with sequential decoding allows a virtually limitless number of codes to be generated.

As previously described, the DBL can be any agent that binds to the IBL. In a preferred embodiment, a single DBL is labeled with a pre-determined ratio of colors. This ratio is varied for each DBL thus allowing for a unique "hue" for each DBL labeled as such. Following treatment of the beads with the DBL, the bead is analyzed to determine the "hue" associated with each bead, thereby identifying the bead with its associated bioactive agent.

For instance, with four primary colors and two intensity levels (color is present or absent), fifteen different hues/stage are possible. If four dyes and three different intensity levels are used (absent, half-present, fully present), then 73 different hues/stage are possible. In this case, acquisition of only 4 color images is sufficient to obtain information on 73 different coding hues.

In a preferred embodiment, the present invention provides array compositions comprising a first substrate with a surface comprising discrete sites. Preferred embodiments utilize a population of microspheres distributed on the sites, and the population comprises at least a first and a second subpopulation. Each subpopulation comprises a bioactive agent, and, in addition, at least one optical dye with a given pKa. The pKas of the different optical dyes are different.

In a preferred embodiment, when for example the array comprises cloned nucleic acids, there are several methods that can be used to decode the arrays. In a preferred embodiment, when some sequence information about the cloned nucleic acids is known, specific decoding probes can be made as is generally outlined herein.

In a preferred embodiment, "random" decoding probes can be made. By sequential hybridizations or the use of multiple labels, as is outlined above, a unique hybridization pattern can be generated for each sensor element. This allows all the beads representing a given clone to be identified as belonging to the same group. In general, this is done by using random or partially degenerate decoding probes, that bind in a sequence-dependent but not highly sequence-specific manner. The process can be repeated a number of times, each time using a different labeling entity, to generate a different pattern of signals based on quasi-specific interactions. In this way, a unique optical signature is eventually built up for each sensor element. By applying pattern recognition or clustering algorithms to the optical signatures, the beads can be grouped into sets that share the same signature (i.e. carry the same probes).

In order to identify the actual sequence of the clone itself, additional procedures are required; for example, direct sequencing can be done. By using an ordered array containing the clones, such as a spotted cDNA array, a "key" can be generated that links a hybridization pattern to a specific clone whose position in the set is known. In this way the clone can be recovered and further characterized.

Alternatively, clone arrays can be decoded using binary decoding with vector tags. For example, partially randomized oligos are cloned into a nucleic acid vector (e.g. plasmid, phage, etc.). Each oligonucleotide sequence consists of a subset of a limited set of sequences. For example, if the limits set comprises 10 sequences, each oligonucleotide may have some subset (or all of the 10) sequences. Thus each of the 10 sequences can be present or absent in the oligonucleotide. Therefore, there are $2^{10}$ or 1,024 possible combinations. The sequences may overlap, and minor variants can also be represented (e.g. A, C, T and G substitutions) to increase the number of possible combinations. A nucleic acid library is cloned into a vector containing the random code sequences. Alternatively, other methods such as PCR can be used to add the tags. In this way it is possible to use a small number of oligo decoding probes to decode an array of clones.

In a preferred embodiment, discriminant analysis and cluster algorithms and computer apparatus are used to analyze the decoding data from the arrays of the invention. The potentially large number of codes utilized in the invention, coupled with the use of different intensities and "hues" of fluorophores in multi-step decoding processes requires good classification of the data. The data, particularly intensity data, is acquired in a multi-step process during which beads are reversibly labeled (for example by hybridizing dye-labeled complementary decoding oligonucleotides to the IBL probes on the beads, or the formation of binding ligand pairs for non-nucleic acid IBL-DBL pairs) with different colors or mixtures of colors ("hues") at each stage. The challenge is to accurately classify a bead as to which color with which it was painted at each step. The more closely related the labels are to one another (as determined by the optical imaging system), the more difficult the classification.

The proximity of the dyes as seen by the imaging system is determined by the spectral properties of the decoding dyes and the spectral channel separation of the imaging system. Better color separation is achieved by employing fluorescent dyes with narrow emission spectra, and by employing an optical system with narrow band pass excitation and emission filters which are designed to excite the dye "on peak" and measure its emission "on peak". The process of optically imaging the dyes on the beads is similar to the human vision process in which our brain sees color by measuring the ratio of excitation in the three different cone types within our eye. However, with an optical imaging system, the number of practical color channels is much greater than the three present in the human eye. CCD based imaging systems can "see" color from 350 nm up to 850 nm whereas the cones in the eye are tuned to the visible spectrum from 500-600 nm.

The problem of decoding bead arrays is essentially a discriminant analysis classification problem. Thus, in a preferred embodiment, an analysis of variance in hyperspectral alpha space is performed. on a known set of bead colors or hues. The center of the bead clusters in alpha space are termed the centroids of the clusters, and the scatter of the points within a cluster determines the spread of the cluster. A robust classification scheme requires that the distance between the centroids of the different bead classes (hues) is much greater than the spread of any cluster class. Moreover, the location of the centroids should remain invariant from fiber to fiber and from experiment to experiment. Thus, in a preferred embodiment, a hue "zone" is defined as a region in alpha space surrounding the hue centroid and extending out to the spread radius of the cluster. Given a reference set of hue centroids and spread radii, as determined empirically, the classification of a new set of data can be accomplished by asking whether a given bead point falls closest to or within the "zone" of a hue cluster. This is accomplished by calculating the Mahalanobis distance (in this case, it is simply a Euclidean distance metric) of the bead point from the centroids of the different hue classes. For the data shown in FIG. 3, the location of the centroids and their distances from one another are indicated in Table 2.

TABLE 2

| dye/channel | Centroid position | | | | Distance between centroids | | | |
| --- | --- | --- | --- | --- | --- | --- | --- | --- |
| | Blue | Green | Yellow | Red | Bod-439 | Bod-R6G | Bod-564 | Bod-TXR |
| Bod-493 | 0.63 | 0.22 | 0.11 | 0.03 | 0.00 | | | |
| Bod-R6G | 0.03 | 0.51 | 0.37 | 0.09 | 0.72 | 0.00 | | |
| Bod-564 | 0.06 | 0.04 | 0.57 | 0.32 | 0.81 | 0.55 | 0.00 | |
| Bod-TXR | 0.09 | 0.05 | 0.04 | 0.82 | 0.99 | 0.93 | 0.73 | 0.00 |

For classifying the different beads into a particular hue class, a Euclidean distance cutoff of 0.3 was chosen. The closest two centroids, the Bod-R6G and Bod-564 (dist=0.55), have a slight overlap in their decoding zones when using a Euclidean or Mahalanobis distance of 0.3. An improvement in classification can be achieved by decreasing this distance, and by weighting the different coordinate axes appropriately.

Accordingly, the present invention provides computer methods for analyzing and classifying the color of a bead. The classification of the color of the bead is done by viewing the bead in hyperspectral "alpha" space ($a_1=I_1/SI_i$, $a_2=I_2/SI_i$, $a_3=I_3/SI_i$, etc.) in which each coordinate axis represents the fraction of the bead intensity within a given imaging channel. For instance, if four imaging channels are used to image the beads, the color or hue of a bead can be represented by a point in 3-D alpha space (the fourth dimension is not necessary since $Sa_i=1$). Given a set of different primary dyes by which to label the beads, the number of hues that can be generated from these dyes is unlimited since the dyes can be combined in varying ratios and in varying combinatorial patterns. The number of practical hues is experimentally determined by the separation of the different hue clusters in hyperspectral alpha space.

FIG. 3 shows a hyperspectral alpha plot of beads labeled with four different hues imaged in four separate imaging channels. Note that the beads form four distinct clusters. The fact that these four clusters are well separated allows a robust decode classification scheme to be implemented.

In a preferred embodiment, a quality control analysis of the decoding process is done. This is achieved by performing a cluster analysis of alpha space for each decoding stage. The number of clusters determined will be fixed by the expected number of hues. The positions of the cluster centroids will be monitored and any deviations from the expected position will be noted.

Thus the invention provides an apparatus for decoding the arrays of the invention. In addition to the compositions outlined herein, the apparatus includes a central processing unit which communicates with a memory and a set of input/output devices {e.g., keyboard, mouse, monitor, printer, etc.} through a bus. The general interaction between a central processing unit, a memory, input/output devices, and a bus is known in the art. One aspect of the present invention is directed toward the hyperspectral "alpha" space classification system stored in the memory.

The classification system program includes a data acquisition module that receives data from the optical reader or confocal microscope (or other imaging system). In general, the classification program also includes an analysis module, that can analyze the variance in hyperspectral alpha space, calculate the centroids of the clusters, calculate the scatter of the cluster (the spread) and define the hue zone and distance cutoff. In general, the analysis module will further determine whether a data point falls within the hue zone by calculating the Mahalanobis distance.

Finally, the analysis module will analyze the different sequential decoding information to finally assign a bioactive agent to a bead location.

In this way, sequential decoding steps are run, with each step utilizing the discriminant analysis calculations to assign each bead in the array to a hue cluster at each step. The buildup of the sequential decoding information allows the correlation of the location of a bead and the chemistry contained on it.

Once made, the compositions of the invention find use in a number of applications. In a preferred embodiment, the compositions are used to probe a sample solution for the presence or absence of a target analyte, including the quantification of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications, as is generally outlined in U.S. Ser. Nos. 60/160,027; 60/161,148; 09/425,633; and 60/160,917, all of which are expressly incorporated herein by reference.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmanella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art; in particular, single base extension (SBE) and pyrosequencing techniques are particularly useful with the compositions of the invention.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$ with less than about $10^{-5}$ to $10^{-9}$ $M^{-1}$ being preferred and less than about $10^{-7}$-$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological. conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art.

Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

In addition, when the target analyte and the DBL both bind to the agent, it is also possible to do detection of non-labelled target analytes via competition of decoding.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal—this can be detected during decoding. The omission of one or more agents from multiple arrays can also be detected. An advantage of this quality control procedure is that it can be implemented immediated prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DBLs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different fluorophores. In this way, signal as a response to concentration can be measured for each bead. This calibration can be carried out just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, in a preferred embodiment, the methods of the invention are useful in quantitation in assay development. Major challenges of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, this can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are chosen empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

In a preferred embodiment, cDNA arrays are made for RNA expression profiling. In this embodiment, individual cDNA clones are amplified (for example, using PCR) from cDNA libraries propagated in a host-vector system. Each amplified DNA is attached to a population of beads. Different populations are mixed together, to create a collection of beads representing the cDNA library. The beads are arrayed, decoded as outlined above, and used in an assay (although as outlined herein, decoding may occur after assay as well). The assay is done using RNA samples (whole cell or mRNA) that are extracted, labeled if necessary, and hybridized to the array. Comparative analysis allows the detection of differences in the expression levels of individual RNAs. Comparison to an appropriate set of calibration standards allows quantification of absolute amounts of RNA.

The cDNA array can also be used for mapping, e.g. to map deletions/insertions or copy number changes in the genome, for example from tumors or other tissue samples. This can be done by hybridizing genomic DNA. Instead of cDNAs (or ESTs, etc.), other STS (sequence tagged sites), including random genomic fragments, can also be arrayed for this purpose.

All references cited herein are incorporated by reference in their entirety.

What is claimed is:

1. A robotic system for manipulating arrays, said system comprising:
   a multiwell plate;
   a base plate having at least one array component associated therewith, said at least one array component comprising a plurality of projections, each projection having an end comprising a surface, said surface having an array of different nucleic acids distributed thereon, wherein said array of different nucleic acids comprises nucleic acids having different nucleotide sequences, and wherein the projections are configured to be dipped into wells of said multiwell plate; and
   a plate handler for dipping the projections of said at least one array component into wells of said multiwell plate.

2. The robotic system of claim 1 further comprising a fluidics system.

3. The robotic system of claim 2, wherein said fluidics system and said plate handler are integrated.

4. The robotic system of claim 2, wherein said fluidics system and said plate handler are separated.

5. The robotic system of claim 2 further comprising a controller for programming processes performed by said plate handler or fluidics system.

6. The robotic system of claim 5, wherein said controller is programmed with a script that instructs said plate handler to dip said projections of said at least one array component into wells of said multiwell plate.

7. The robotic system of claim 1, wherein manipulation of said arrays is partially automated.

8. The robotic system of claim 1, wherein manipulation of said arrays is fully automated.

9. The robotic system of claim 1, wherein said base plate is a holder comprising at least one depression into which said array component is inserted.

10. The robotic system of claim 1, wherein said base plate comprises a plate to which said array component is attached.

11. The robotic system of claim 1, wherein said at least one array component comprises a plurality of array components each comprising a plurality of projections.

12. The robotic system of claim 1, wherein said base plate and said multiwell plate each further comprises one or more alignment moieties.

13. The robotic system of claim 12, wherein said one or more alignment moieties on said multiwell plate are female fittings and said one or more alignment moieties on said base plate are male fittings.

14. The robotic system of claim 13, wherein said one or more male fittings are inserted into said one or more female fittings.

15. The robotic system of claim 14, wherein each array comprises at least 1000 different nucleic acids per square centimeter.

16. The robotic system of claim 15, wherein said surface is a glass surface.

17. The robotic system of claim 15, wherein said surface is planar.

18. The robotic system of claim 17, wherein said nucleic acids are attached to planar surface in an ordered arrangement.

19. The robotic system of claim 18, wherein said arrays are substantially identical to each other.

20. The robotic system of claim 19, wherein said multiwell plate comprises 96 wells.

21. The robotic system of claim 20, wherein said at least one array component comprises 96 projections.

22. The robotic system of claim 20, wherein said at least one array component comprises less than 96 projections.

23. The robotic system of claim 20, wherein said array is made by a spotting, printing or photolithographic technique.

24. The robotic system of claim 20, wherein said projections are made of a material that resists the transmission of light.

25. The robotic system of claim 1, wherein said projections are not fiber optic bundles.

26. The robotic system of claim 25, wherein the configuration orients the surface having the nucleic acids distributed thereon such that said surface faces a bottom of a well in the multiwell plate.

27. The robotic system of claim 26, wherein said nucleic acids are present at sites.

28. The robotic system of claim 27, wherein the sites are contiguous.

29. A robotic system for manipulating arrays, said system comprising:
   a multiwell plate;
   a base plate having at least one array component associated therewith, said at least one array component comprising a plurality of projections, each projection having an end comprising a surface, said surface having an array of different nucleic acids distributed thereon, wherein said array of different nucleic acids comprises nucleic acids having different nucleotide sequences, and wherein the projections are configured to be dipped into wells of said multiwell plate;
   a plate handler for dipping the projections of said at least one array component into wells of said multiwell plate; and
   a controller programmed for controlling processes performed by said robotic system, wherein said processes comprise hybridization of the nucleic acids to target nucleic acids, washing the array of different nucleic acids and acquiring an image of the array of different nucleic acids.

30. The robotic system of claim 29, wherein said processes controlled by the controller further comprise signal amplification using an antibody.

31. The robotic system of claim 29 further comprising a fluidics system adapted to provide fluids to wells of said multiwell plate.

32. The robotic system of claim 29, wherein said controller is programmed with a script that instructs said plate handler to dip said projections of said at least one array component into wells of said multiwell plate.

33. The robotic system of claim 29, wherein said base plate is a holder comprising at least one depression into which said array component is inserted.

34. The robotic system of claim 29, wherein each array comprises at least 1000 different nucleic acids per square centimeter.

35. The robotic system of claim 29, wherein said base plate and said multiwell plate each further comprises one or more alignment moieties.

36. The robotic system of claim 29, wherein said multiwell plate comprises 96 wells.

37. The robotic system of claim 36, wherein said at least one array component comprises less than 96 projections.

38. The robotic system of claim 29 further comprising a thermoregulating system.

39. The robotic system of claim 29, wherein the vertical center axis of a projection is aligned with the center axis of a well in the multiwell plate.

40. The robotic system of claim 29 further comprising a CCD camera to acquire said image.

41. The robotic system of claim 29, wherein said plate handler fits said projections within said wells of said multiwell plate.

42. The robotic system of claim 29 further comprising a hybridization chamber that encloses said array of different nucleic acids.

43. The robotic system of claim 42, wherein the hybridization chamber encloses the array of different nucleic acids and the multiwell plate.

44. The robotic system of claim 29, wherein the robotic system is a modular system.

45. The robotic system of claim 29, wherein said projections are not fiber optic bundles.

46. The robotic system of claim 45, wherein the configuration orients the surface having the nucleic acids distributed thereon such that said surface faces a bottom of a well in the multiwell plate.

47. The robotic system of claim 46, wherein said nucleic acids are present at sites.

48. The robotic system of claim 47, wherein the sites are contiguous.

49. A robotic system for manipulating arrays, said system comprising:
 a multiwell plate;
 a base plate having at least one array component placed thereon, said at least one array component comprising at least one projection, each projection having an end comprising a surface, said surface having an array of different nucleic acids attached thereto, wherein said array of different nucleic acids comprises nucleic acids having different nucleotide sequences, and wherein the at least one projection is configured to be dipped into wells of said multiwell plate; and
 a plate handler for dipping the projections of said at least one array component into wells of said multiwell plate.

50. The robotic system of claim 49, wherein the projections are made of a material that resists the transmission of light.

51. The robotic system of claim 49, wherein the vertical center axis of the at least one projection is aligned with the center axis of a well in the multiwell plate.

52. The robotic system of claim 49, wherein said at least one array component comprises a plurality of projections.

53. The robotic system of claim 52 further comprising a CCD camera.

54. The robotic system of claim 53 further comprising a fluidics system.

55. The robotic system of claim 54 further comprising a controller for programming processes performed by said plate handler or fluidics system.

56. The robotic system of claim 55, wherein said controller is programmed with a script that instructs said plate handler to dip said projections of said at least one array component into wells of said multiwell plate.

57. The robotic system of claim 56, wherein said base plate is a holder comprising at least one depression into which said array component is inserted.

58. The robotic system of claim 57 further comprising a thermoregulating system.

59. The robotic system of claim 58, wherein said multiwell plate comprises 96 wells.

60. The robotic system of claim 59, wherein said at least one array component comprises less than 96 projections.

61. The robotic system of claim 59, wherein said at least one array component comprises a plurality of array components each comprising a plurality of projections.

62. The robotic system of claim 59, wherein said base plate and said multiwell plate each further comprises one or more alignment moieties.

63. The robotic system of claim 49, wherein said plate handler fits said projections within said wells of said multiwell plate.

64. The robotic system of claim 49 further comprising a hybridization chamber that encloses said array of different nucleic acids.

65. The robotic system of claim 64, wherein the hybridization chamber encloses the array of different nucleic acids and the multiwell plate.

66. The robotic system of claim 49, wherein the system is a modular system.

67. The robotic system of claim 49, wherein said projections are not fiber optic bundles.

68. The robotic system of claim 67, wherein the configuration orients the surface having the nucleic acids distributed thereon such that said surface faces a bottom of a well in the multiwell plate.

69. The robotic system of claim 68, wherein said nucleic acids are present at sites.

70. The robotic system of claim 69, wherein the sites are contiguous.

* * * * *